US012601017B2

(12) United States Patent
Poon et al.

(10) Patent No.:  US 12,601,017 B2
(45) Date of Patent:  Apr. 14, 2026

(54) MOLECULAR DETECTION OF NOVEL CORONAVIRUSES

(71) Applicant: The University of Hong Kong, Hong Kong (CN)

(72) Inventors: Leo LM Poon, Hong Kong (CN); Malik Peiris, Hong Kong (CN); Daniel K.W. Chu, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 1070 days.

(21) Appl. No.: 17/545,818

(22) Filed: Dec. 8, 2021

(65) Prior Publication Data

US 2022/0243290 A1     Aug. 4, 2022

Related U.S. Application Data

(60) Provisional application No. 63/143,930, filed on Jan. 31, 2021.

(51) Int. Cl.
| | |
|---|---|
| *C12Q 1/70* | (2006.01) |
| *C12N 15/10* | (2006.01) |
| *C12Q 1/6804* | (2018.01) |
| *C12Q 1/6851* | (2018.01) |
| *C12Q 1/686* | (2018.01) |

(52) U.S. Cl.
CPC ............. *C12Q 1/701* (2013.01); *C12Q 1/686* (2013.01); *C12Q 2600/158* (2013.01)

(58) Field of Classification Search
CPC .. C12Q 1/701; C12Q 2600/158; C12Q 1/686; C12Q 2600/16; C12Q 1/6844
See application file for complete search history.

(56) References Cited

U.S. PATENT DOCUMENTS

| | | | | |
|---|---|---|---|---|
| 2005/0100885 A1* | 5/2005 | Crooke | .............. | C12N 15/1137 |
| | | | | 435/5 |
| 2023/0174590 A1 | 6/2023 | Hachim et al. | | |

FOREIGN PATENT DOCUMENTS

| | | | |
|---|---|---|---|
| CN | 110951756 A | | 4/2020 |
| CN | 111024954 A | | 4/2020 |
| CN | 111041089 A | | 4/2020 |
| CN | 111060691 A | | 4/2020 |
| CN | 111394522 A | * | 7/2020 |
| CN | 111560481 A | * | 8/2020 |
| WO | 2017039967 A1 | | 3/2017 |

OTHER PUBLICATIONS

No et al., Genbank Ascession No. MN908947.3, 2020.*
Chan, et al., "The emergence of human coronavirus EMC: how scared should we be?", mBio, 4(2):e00191-13 (2013).

Chu, et al., "MERS coronaviruses from camels in Africa exhibit region-dependent genetic diversity", PNAS, 115(12):3144-9 (2018).
Corman, et al., "Detection of 2019 novel coronavirus (2019-nCov) by real-time RT-PCR", Euro Surveill., 23-30 (2020).
Cui, et al., "Origin and evolution of pathogenic coronaviruses", Nat. Rev. Microbiol., 17:181-92 (2019).
De Wit, et al., "SARS and MERS: recent insights into emerging coronaviruses", Nat. Rev. Microbiol., 14(8):523-34 (2016).
Donnelly, et al., "Worldwide Reduction in MERS Cases and Deaths since 2016", Emerg. Infect. Dis., 25(9):1758-60 (2019).
Guan, et al., "Isolation and characterization of viruses related to the SARS coronavirus from animals in southern China", Science, 302(5643):276-8 (2003).
Hemida, et al., "Middle East Respiratory Syndrome (MERS) coronavirus seroprevalence in domestic livestock in Saudi Arabia, 2010 to 2013", Euro Surveill., 18(50):20659 (2013).
Hu, et al., "Characteristics of SARS-CoV-2 and COVID-19", Nat. Rev. Microbiol., 19(3):141-154 (2021).
Hu, et al., "Discovery of a rich gene pool of bat SARS-related coronaviruses provides new insights into the origin of SARS coronavirus", PLoS Pathog., 13(11):e1006698 (2017).
Jonsson, et al., "Real-time polymerase chain reaction as a rapid and efficient alternative to estimation of picornavirus titers by tissue culture infectious dose 50% or plaque forming units", Microbiol. Immunol., 53(3):149-154 (2009).
Kumar, et al., "MEGA X: Molecular Evolutionary Genetics Analysis across Computing Platforms", Mol. Biol. Evol., 35(6):1547-9 (2018).
Poon, et al., "The aetiology, origins, and diagnosis of severe acute respiratory syndrome", Lancet Infect Dis.,4(11):663-71 (2004).
Reusken, et al., "Middle East Respiratory Syndrome coronavirus (MERS-CoV) serology in major livestock species in an affected region in Jordan, Jun. to Sep. 2013", Euro. Surveill., 18(50):20662 (2013).
Rota, et al., "Characterization of a Novel Coronavirus Associated with Severe Acute Respiratory Syndrome", Science, 1-10 (2003).
Simons et al., "A mRNA PCR for the diagnosis of feline infectious peritonitis", J. Virol. Methods, 124(1):111-6 (2005).

(Continued)

*Primary Examiner* — Barry A Chestnut
(74) *Attorney, Agent, or Firm* — Pabst Patent Group LLP

(57) ABSTRACT

Systems for sensitive and accurate detection of sarbecoviruses in samples from human sputum have been established. The systems can rapidly and effectively diagnose patients having suspected coronavirus infections. The systems employ Reverse-Transcription Quantitative Polymerase Chain Reaction (RT-qPCR) to identify and quantify nucleic acids specific to sarbecoviruses within samples from human patients. The systems identify viral RNAs specific for the N and ORF1 genes using a two-step real-time PCR and the SYBR Green detection method. Compositions and methods for reproducibly detecting and quantifying concentrations of sarbecoviruses with a dynamic range of at least seven orders of magnitude ($2\times10^{-4}$-2000 $TCID_{50}$/reaction) are described. The compositions and methods enable rapid early diagnosis of patients, as well as development of databases of patient viral titres and infectious dosages.

20 Claims, 2 Drawing Sheets

Specification includes a Sequence Listing.

(56) References Cited

OTHER PUBLICATIONS

Wang, et al., "SARS-CoV Infection in a Restaurant from Palm Civet", Emerg. Infect. Dis., 11(12):1860-5 (2005).

World Health Organization, "Detection of 2019 novel coronavirus (2019-nCoV) in suspected human cases by RT-PCR", retrieved from webpage, <who.int/docs/default-source/coronaviruse/peiris-protocol-16-1-20.pdf? sfvrsn=af1aac73_4/>, Accessed Feb. 27, 2023.

World Health Organization, "Novel Coronavirus (2019-nCoV)", Situation report—1, retrieved from webpage, <who.int/docs/default-source/coronaviruse/situation-reports/20200121-sitrep-1-2019-ncov.pdf? sfvrsn=20a99c10_4>, Jan. 20, 2020, retrieved Feb. 27, 2023.

World Health Organization., "Novel Coronavirus(2019-nCoV), Situation report—2", retrieved from internet, <https://apps.who.int/iris/handle/10665/330761>, Jan. 20, 2020, retrieved Feb. 27, 2023.

Zhou, et al., "Discovery of a novel coronavirus associated with the recent pneumonia outbreak in 2 humans and its potential bat origin", bioRxiv, Preprint at webpage, <biorxiv.org/content/10.1101/2020.01.22.914952v1>, posted Jan. 23, 2020, retrieved Feb. 27, 2023.

International Search Report received for PCT Patent Application No. PCT/CN2021/090684, mailed on Jul. 29, 2021, 6 pages.

Hachim , et al., "Beyond the Spike: identification of viral targets of the antibody responses to SARS-CoV-2 in COVID-19 patients", MedRxiv, doi: https://doi.org/10.1101/2020.04.30.20085670, May 2, 2020, 33 pages.

Hachim , et al., "ORF8 and ORF3b antibodies are accurate serological markers of early and late SARS-CoV-2 infection", Nat Immunol., vol. 21, No. 10, Oct. 2020, pp. 1293-1301.

Hachim , et al., "The SARS-CoV-2 antibody landscape is lower in magnitude for structural proteins, diversified for accessory proteins and stable long-term in children,", MedRxiv, doi: https://doi.org/10.1101/2021.01.03.21249180, Jan. 4, 2021, 42 pages.

Wu , et al., "A New Coronavirus Associated with Human Respiratory Disease in China", Nature, vol. 579, No. 7798, Mar. 12, 2020, pp. 265-269.

Singh, et al., "Designing a multi-epitope peptide based vaccine against SARS-CoV-2", Biorxiv, doi: https://doi.org/10.1101/2020.04.15.040618, Apr. 16, 2020, 25 pages.

* cited by examiner

ORF1b assay

N assay

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: forward primer sequence for the SARS-CoV-2
      virus ORF1b gene
<220> FEATURE:
<221> NAME/KEY: misc_feature
<222> LOCATION: (6)..(6)
<223> OTHER INFORMATION: Y=C or T
<220> FEATURE:
<221> NAME/KEY: misc_feature
<222> LOCATION: (12)..(12)
<223> OTHER INFORMATION: R=A or G

<400> SEQUENCE: 1
tggggyttta crggtaacct                                                    20

<210> SEQ ID NO 2
<211> LENGTH: 21
<212> TYPE: DNA
<213> ORGANISM: Artificial Sequence
<220> FEATURE:
<223> OTHER INFORMATION: reverse primer sequence for the SARS-CoV-2
      virus ORF1b gene
<220> FEATURE:
<221> NAME/KEY: misc_feature
<222> LOCATION: (4)..(4)
<223> OTHER INFORMATION: R=A or G

<400> SEQUENCE: 2
aacrcgctta acaaagcact c                                                  21

<210> SEQ ID NO 3
<211> LENGTH: 24
<212> TYPE: DNA
<213> ORGANISM: Artificial Sequence
<220> FEATURE:
<223> OTHER INFORMATION: probe for detecting the presence of the
      amplified gene fragment

<400> SEQUENCE: 3
tagttgtgat gcwatcatga ctag                                               24
```

<210> SEQ ID NO 4
<211> LENGTH: 22
<212> TYPE: DNA
<213> ORGANISM: Artificial Sequence
<220> FEATURE:
<223> OTHER INFORMATION: forward primer sequence for the SARS-CoV-2
      virus N gene

<400> SEQUENCE: 4
taatcagaca aggaactgat ta                                            22

<210> SEQ ID NO 5
<211> LENGTH: 19
<212> TYPE: DNA
<213> ORGANISM: Artificial Sequence
<220> FEATURE:
<223> OTHER INFORMATION: reverse primer sequence for the SARS-CoV-2
      virus N gene

<400> SEQUENCE: 5
cgaaggtgtg acttccatg                                                19

<210> SEQ ID NO 6
<211> LENGTH: 20
<212> TYPE: DNA
<213> ORGANISM: Artificial Sequence
<220> FEATURE:
<223> OTHER INFORMATION: probe for detecting the presence of the
      amplified gene fragment

<400> SEQUENCE: 6
gcaaattgtg caatttgcgg                                               20

<210> SEQ ID NO 7
<211> LENGTH: 21291
<212> TYPE: DNA
<213> ORGANISM: Severe Acute Respiratory Syndrome Coronavirus 2

<400> SEQUENCE: 7
atggagagcc ttgtccctgg tttcaacgag aaaacacacg tccaactcag tttgcctgtt     60
ttacaggttc gcgacgtgct cgtacgtggc tttggagact ccgtggagga ggtcttatca    120
gaggcacgtc aacatcttaa agatggcact tgtggcttag tagaagttga aaaaggcgtt    180
ttgcctcaac ttgaacagcc ctatgtgttc atcaaacgtt cggatgctcg aactgcacct    240
catggtcatg ttatggttga ctggtagca gaactcgaag cattcagta cggtcgtagt      300 ggtgagacac ttggtgtcct tgtccctcat gtgggcgaaa taccagtggc ttaccgcaag    360
gttcttcttc gtaagaacgg taataaagga gctggtggcc atagttacgg cgccgatcta    420
aagtcatttg acttaggcga cgagcttggc actgatcctt atgaagattt tcaagaaaac    480
tggaacacta acatagcag tggtgttacc cgtgaactca tgcgtgagct taacggaggg     540
gcatacactc gctatgtcga taacaacttc tgtggccctg atggctaccc tcttgagtgc    600
attaaagacc ttctagcacg tgctggtaaa gcttcatgca ctttgtccga caactggac    660 tttattgaca ctaagagggg tgtatactgc tgccgtgaac atgagcatga aattgcttgg    720
tacacggaac gttctgaaaa gagctatgaa ttgcagacac cttttgaaat taaattggca    780
aagaaatttg acaccttcaa tgggg aatgt ccaaattttg tatttccctt aaattccata   840
atcaagacta ttcaaccaag ggttgaaaag aaaaagcttg atggctttat gggtagaatt    900
cgatctgtct atccagttgc gtcaccaaat gaatgcaacc aaatgtgcct ttcaactctc    960

```
atgaagtgtg atcattgtgg tgaaacttca tggcagacgg gcgatttttgt taaagccact    1020 tgcgaatttt gtggcactga gaatttgact aaagaaggtg ccactacttg tggttactta    1080
ccccaaaatg ctgttgttaa aatttattgt ccagcatgtc acaattcaga agtaggacct    1140
gagcatagtc ttgccgaata ccataatgaa tctggcttga aaaccattct tcgtaagggt    1200
ggtcgcacta ttgcctttgg aggctgtgtg ttctcttatg ttggttgcca taacaagtgt    1260
gcctattggg ttccacgtgc tagcgctaac ataggttgta accatacagg tgttgttgga    1320
gaaggttccg aaggtcttaa tgacaacctt cttgaaatac tccaaaaaga gaaagtcaac    1380
atcaatattg ttggtgactt taaacttaat gaagagatcg ccattatttt ggcatctttt    1440
tctgcttcca caagtgcttt tgtggaaact gtgaaaggtt tggattataa agcattcaaa    1500
caaattgttg aatcctgtgg taattttaaa gttacaaaag gaaaagctaa aaaaggtgcc    1560
tggaatattg gtgaacagaa atcaatactg agtcctcttt atgcatttgc atcagaggct    1620
gctcgtgttg tacgatcaat tttctcccgc actcttgaaa ctgctcaaaa ttctgtgcgt    1680
gttttacaga aggccgctat aacaatacta gatggaattt cacagtattc actgagactc    1740
attgatgcta tgatgttcac atctgatttg gctactaaca atctagttgt aatggcctac    1800
attacaggtg gtgttgttca gttgacttcg cagtggctaa ctaacatctt tggcactgtt    1860
tatgaaaaac tcaaacccgt ccttgattgg cttgaagaga agtttaagga aggtgtagag    1920
tttcttagag acggttggga aattgttaaa tttatctcaa cctgtgcttg tgaaattgtc    1980
ggtggacaaa ttgtcacctg tgcaaaggaa attaaggaga gtgttcagac attctttaag    2040
cttgtaaata aattttttggc tttgtgtgct gactctatca ttattggtgg agctaaactt    2100
aaagccttga atttaggtga aacatttgtc acgcactcaa agggattgta cagaaagtgt    2160
gttaaatcca gagaagaaac tggcctactc atgcctctaa aagccccaaa agaaattatc    2220
ttcttagagg gagaaacact tcccacagaa gtgttaacag aggaagttgt cttgaaaact    2280
ggtgatttac aaccattaga acaacctact agtgaagctg ttgaagctcc attggttggt    2340
acaccagttt gtattaacgg gcttatgttg ctcgaaatca aagacacaga aaagtactgt    2400
gcccttgcac ctaatatgat ggtaacaaac aataccttca cactcaaagg cggtgcacca    2460
acaaaggtta cttttggtga tgacactgtg atagaagtgc aaggttacaa gagtgtgaat    2520 atcactttttg aacttgatga aaggattgat aaagtactta atgagaagtg ctctgcctat    2580
acagttgaac tcggtacaga agtaaatgag ttcgcctgtg ttgtggcaga tgctgtcata    2640
aaaactttgc aaccagtatc tgaattactt acaccactgg gcattgattt agatgagtgg    2700
agtatggcta catactactt atttgatgag tctggtgagt ttaaattggc ttcacatatg    2760
tattgttctt ctacccctcc agatgaggat aagaagaag gtgattgtga agaagaagag    2820
tttgagccat caactcaata tgagtatggt actgaagatg attaccaagg taaacctttg    2880
gaatttggtg ccacttctgc tgctcttcaa cctgaagaag agcaagaaga agattggtta    2940
gatgatgata gtcaacaaac tgttggtcaa caagacggca gtgaggacaa tcagacaact    3000
actattcaaa caattgttga ggttcaacct caattagaga tggaacttac accagttgtt    3060
cagactattg aagtgaatag tttttagtggt tatttaaaac ttactgacaa tgtatacatt    3120
aaaaatgcag acattgtgga agaagctaaa aaggtaaaac caacagtggt tgttaatgca    3180
gccaatgttt accttaaaca tggaggaggt gttgcaggag ccttaaataa ggctactaac    3240
aatgccatgc aagttgaatc tgatgattac atagctacta atggaccact aaagtggggt    3300
```

```
ggtagttgtg ttttaagcgg acacaatctt gctaaacact gtcttcatgt tgtcggccca   3360
aatgttaaca aaggtgaaga cattcaactt cttaagagtg cttatgaaaa ttttaatcag   3420
cacgaagttc tacttgcacc attattatca gctggtattt ttggtgctga ccctatacat   3480
tctttaagag tttgtgtaga tactgttcgc acaaatgtct acttagctgt ctttgataaa   3540
aatctctatg acaaacttgt ttcaagcttt ttggaaatga agagtgaaaa gcaagttgaa   3600
caaaagatcg ctgagattcc taaagaggaa gttaagccat ttataactga aagtaaacct   3660
tcagttgaac agagaaaaca agatgataag aaaatcaaag cttgtgttga agaagttaca   3720
acaactctgg aagaaactaa gttcctcaca gaaaacttgt tactttatat tgacattaat   3780
ggcaatcttc atccagattc tgccactctt gttagtgaca ttgacatcac tttcttaaag   3840
aaagatgctc catatatagt gggtgatgtt gttcaagagg gtgtttttaac tgctgtggtt   3900 ataccctacta aaaaggctgg tggcactact gaaatgctag cgaaagcttt gagaaaagtg   3960
ccaacagaca attatataac cacttacccg ggtcagggtt aaaatggtta cactgtagag   4020
gaggcaaaga cagtgcttaa aaagtgtaaa agtgcctttt acattctacc atctattatc   4080
tctaatgaga agcaagaaat tcttggaact gtttcttgga atttgcgaga aatgcttgca   4140
catgcagaag aaacacgcaa attaatgcct gtctgtgtgg aaactaaagc catagtttca   4200
actatacagc gtaaatataa gggtattaaa atacaagagg gtgtggttga ttatggtgct   4260
agattttact tttacaccag taaaacaact gtagcgtcac ttatcaacac acttaacgat   4320
ctaaatgaaa ctcttgttac aatgccactt ggctatgtaa cacatggctt aaatttggaa   4380
gaagctgctc ggtatatgag atctctcaaa gtgccagcta cagttctgt ttcttcacct   4440 gatgctgtta cagcgtataa tggttatctt acttcttctt ctaaaacacc tgaagaacat   4500
tttattgaaa ccatctcact tgctggttcc tataaagatt ggtcctattc tggacaatct   4560
acacaactag gtatagaatt tcttaagaga ggtgataaaa gtgtatatta cactagtaat   4620
cctaccacat tccacctaga tggtgaagtt atcacctttg acaatcttaa gacacttctt   4680
tctttgagag aagtgaggac tattaaggtg tttacaacag tagacaacat taacctccac   4740
acgcaagttg tggacatgtc aatgacatat ggacaacagt ttggtccaac ttatttggat   4800
ggagctgatg ttactaaaat aaaacctcat aattcacatg aaggtaaaac attttatgtt   4860
ttacctaatg atgacactct acgtgttgag gctttgagt actaccacac aactgatcct   4920
agttttctgg gtaggtacat gtcagcatta aatcacacta aaaagtggaa ataccacaa   4980 gttaatggtt taacttctat aaatgggca gataacaact gttatcttgc cactgcattg   5040
ttaacactcc aacaaataga gttgaagttt aatccacctg ctctacaaga tgcttattac   5100
agagcaaggg ctggtgaagc tgctaacttt tgtgcactta tcttagccta ctgtaataag   5160
acagtaggtg agttaggtga tgttagagaa acaatgagtt acttgtttca acatgccaat   5220
ttagattctt gcaaaagagt cttgaacgtg tgtgtaaaa cttgtggaca acagcagaca   5280
acccttaagg gtgtagaagc tgttatgtac atgggcacac tttcttatga acaatttaag   5340
aaaggtgttc agataccttg tacgtgtggt aaacaagcta caaatatct agtacaacag   5400 gagtcacctt tgttatgat gtcagcacca cctgctcagt atgaacttaa gcatggtaca   5460
tttacttgtg ctagtgagta cactggtaat taccagtgtg gtcactataa acatataact   5520
tctaaagaaa ctttgtattg catagacggt gctttactta caaagtcctc agaatacaaa   5580
ggtcctatta cggatgtttt ctacaaagaa aacagttaca caacaaccat aaaaccagtt   5640
acttataaat tggatggtgt tgtttgtaca gaaattgacc ctaagttgga caattattat   5700
```

-continued

```
aagaaagaca attcttattt cacagagcaa ccaattgatc ttgtaccaaa ccaaccatat    5760
ccaaacgcaa gcttcgataa tttttaagttt gtatgtgata atatcaaatt tgctgatgat   5820
ttaaaccagt taactggtta taagaaacct gcttcaagag agcttaaagt tacatttttc   5880
cctgacttaa atggtgatgt ggtggctatt gattataaac actacacacc ctctttttaag  5940 aaaggagcta aattgttaca taaacctatt gtttggcatg ttaacaatgc aactaataaa   6000
gccacgtata aaccaaatac ctggtgtata cgttgtcttt ggagcacaaa accagttgaa   6060
acatcaaatt cgtttgatgt actgaagtca gaggacgcgc agggaatgga taatcttgcc   6120
tgcgaagatc taaaaccagt ctctgaagaa gtagtggaaa atcctaccat acagaaagac   6180
gttcttgagt gtaatgtgaa aactaccgaa gttgtaggag acattatact taaaccagca   6240
aataatagtt taaaaattac agaagaggtt ggccacacag atctaatggc tgcttatgta   6300
gacaattcta gtcttactat taagaaacct aatgaattat ctagagtatt aggtttgaaa   6360
acccttgcta ctcatggttt agctgctgtt aatagtgtcc cttgggatac tatagctaat   6420
tatgctaagc cttttcttaa caaagttgtt agtacaacta ctaacatagt tacacggtgt   6480
ttaaaccgtg tttgtactaa ttatatgcct tatttcttta ctttattgct acaattgtgt   6540
acttttacta gaagtacaaa ttctagaatt aaagcatcta tgccgactac tatagcaaag   6600
aatactgtta agagtgtcgg taaattttgt ctagaggctt catttaatta tttgaagtca   6660
cctatttttt ctaaactgat aaatattata atttggtttt tactattaag tgtttgccta   6720
ggttctttaa tctactcaac cgctgcttta ggtgtttaa tgtctaattt aggcatgcct    6780
tcttactgta ctggttacag agaaggctat ttgaactcta ctaatgtcac tattgcaacc   6840
tactgtactg gttctatacc ttgtagtgtt tgtcttagtg gtttagattc tttagacacc   6900
tatccttctt tagaaactat acaaattacc atttcatctt ttaaatggga tttaactgct   6960
tttggcttag ttgcagagtg gttttttggca tatattcttt tcactaggtt ttttctatgta  7020 cttggattgg ctgcaatcat gcaattgttt ttcagctatt ttgcagtaca ttttattagt   7080
aattcttggc ttatgtggtt aataattaat cttgtacaaa tggccccgat ttcagctatg   7140
gttagaatgt acatcttctt tgcatcattt tattatgtat ggaaaagtta tgtgcatgtt   7200
gtagacggtt gtaattcatc aacttgtatg atgtgttaca aacgtaatag agcaacaaga   7260
gtcgaatgta caactattgt taatggtgtt agaaggtcct tttatgtcta tgctaatgga   7320
ggtaaaggct tttgcaaact acacaattgg aattgtgtta attgtgatac attctgtgct   7380
ggtagtacat ttattagtga tgaagttgcg agagacttgt cactacagtt taaaagacca   7440
ataaatccta ctgaccagtc ttcttacatc gttgatagtg ttacagtgaa gaatggttcc   7500
atccatcttt actttgataa agctggtcaa aagacttatg aaagacattc tctctctcat   7560
tttgttaact tagacaacct gagagctaat aacactaaag gttcattgcc tattaatgtt   7620
atagtttttg atggtaaatc aaaatgtgaa gaatcatctg caaaatcagc gtctgtttac   7680
tacagtcagc ttatgtgtca acctatactg ttactagatc aggcattagt gtctgatgtt   7740
ggtgatagtg cggaagttgc agttaaaatg tttgatgctt acgttaatac gttttcatca   7800
acttttaacg taccaatgga aaaactcaaa acactagttg caactgcaga agctgaactt   7860
gcaaagaatg tgtccttaga caatgtctta tctacttttta tttcagcagc tcggcaaggg   7920
tttgttgatt cagatgtaga aactaaagat gttgttgaat gtcttaaatt gtcacatcaa   7980
tctgacatag aagttactgg cgatagttgt aataactata tgctcaccta taacaaagtt   8040
```

-continued

```
gaaaacatga cacccegtga ccttggtgct tgtattgact gtagtgcgcg tcatattaat    8100
gcgcaggtag caaaaagtca caacattgct ttgatatgga acgttaaaga tttcatgtca    8160
ttgtctgaac aactacgaaa acaaatacgt agtgctgcta aaaagaataa cttacctttt    8220
aagttgacat gtgcaactac tagacaagtt gttaatgttg taacaacaaa gatagcactt    8280
aagggtggta aaattgttaa taattggttg aagcagttaa ttaaagttac acttgtgttc    8340
ctttttgttg ctgctatttt ctatttaata acacctgttc atgtcatgtc taaacatact    8400
gacttttcaa gtgaaatcat aggatacaag gctattgatg gtggtgtcac tcgtgacata    8460
gcatctacag atacttgttt tgctaacaaa catgctgatt ttgacacatg gtttagccag    8520
cgtggtggta gttatactaa tgacaaagct tgcccattga ttgctgcagt cataacaaga    8580
gaagtggggt ttgtcgtgcc tggtttgcct ggcacgatat tacgcacaac taatggtgac    8640
tttttgcatt tcttacctag agtttttagt gcagttggta acatctgtta cacaccatca    8700
aaacttatag agtacactga ctttgcaaca tcagcttgtg ttttggctgc tgaatgtaca    8760
atttttaaag atgcttctgg taagccagta ccatattgtt atgataccaa tgtactagaa    8820
ggttctgttg cttatgaaag tttacgccct gacacacgtt atgtgctcat ggatggctct    8880
attattcaat ttcctaacac ctaccttgaa ggttctgtta gagtggtaac aacttttgat    8940
tctgagtact gtaggcacgg cacttgtgaa agatcagaag ctggtgtttg tgtatctact    9000
agtggtagat gggtacttaa caatgattat tacagatctt taccaggagt tttctgtggg    9060
gtagatgctg taaatttact tactaatatg tttacaccac taattcaacc tattggtgct    9120
ttggacatat cagcatctat agtagctggt ggtattgtag ctatcgtagt aacatgcctt    9180
gcctactatt ttatgaggtt tagaagagct tttggtgaat acagtcatgt agttgccttt    9240
aatactttac tattccttat gtcattcact gtactctgtt taacaccagt ttactcattc    9300
ttacctggtg tttattctgt tatttacttg tacttgacat tttatcttac taatgatgtt    9360 tctttttttag cacatattca gtggatggt atgttcacac ctttagtacc tttctggata    9420
acaattgctt atatcatttg tatttccaca aagcatttct attggttctt tagtaattac    9480
ctaaagagac gtgtagtctt taatggtgtt tcctttagta cttttgaaga agctgcgctg    9540
tgcacctttt tgttaaataa agaaatgtat ctaaagttgc gtagtgatgt gctattacct    9600
cttacgcaat ataatagata cttagctctt tataataagt acaagtattt tagtggagca    9660
atggatacaa ctagctacag agaagctgct tgttgtcatc tcgcaaaggc tctcaatgac    9720
ttcagtaact caggttctga tgttctttac caaccaccac aaacctctat cacctcagct    9780
gttttgcaga gtggttttag aaaaatggca ttcccatctg gtaaagttga gggttgtatg    9840
gtacaagtaa cttgtggtac aactacactt aacggtcttt ggcttgatga cgtagtttac    9900
tgtccaagac atgtgatctg cacctctgaa gacatgctta accctaatta tgaagattta    9960
ctcattcgta agtctaatca taatttcttg gtacaggctg gtaatgttca actcaggggtt    10020 attggacatt ctatgcaaaa ttgtgtactt aagcttaagg ttgatacagc caatcctaag    10080
acacctaagt ataagtttgt tcgcattcaa ccaggacaga cttttttcagt gttagcttgt    10140 tacaatggtt caccatctgg tgtttaccaa tgtgctatga ggcccaattt cactattaag    10200
ggttcattcc ttaatggttc atgtggtagt gttggttta acatagatta tgactgtgtc    10260 tcttttttgtt acatgcacca tatggaatta ccaactggag ttcatgctgg cacagactta    10320
gaaggtaact tttatggacc ttttgttgac aggcaaacag cacaagcagc tggtacggac    10380
acaactatta cagttaatgt tttagcttgg ttgtacgctg ctgttataaa tggagacagg    10440
```

-continued

```
tggtttctca atcgatttac cacaactctt aatgacttta accttgtggc tatgaagtac    10500
aattatgaac ctctaacaca agaccatgtt gacatactag gacctctttc tgctcaaact    10560
ggaattgccg ttttagatat gtgtgcttca ttaaaagaat tactgcaaaa tggtatgaat    10620
ggacgtacca tattgggtag tgctttatta gaagatgaat ttacacccttt tgatgttgtt    10680 agacaatgct caggtgttac tttccaaagt gcagtgaaaa gaacaatcaa gggtacacac    10740
cactggttgt tactcacaat tttgacttca cttttagttt tagtccagag tactcaatgg    10800
tctttgttct ttttttttgta tgaaaatgcc tttttacctt ttgctatggg tattattgct    10860
atgtctgctt ttgcaatgat gtttgtcaaa cataagcatg catttctctg tttgtttttg    10920
ttaccttctc ttgccactgt agcttatttt aatatggtct atatgcctgc tagttgggtg    10980
atgcgtatta tgacatggtt ggatatggtt gatactagtt tgtctggttt taagctaaaa    11040
gactgtgtta tgtatgcatc agctgtagtg ttactaatcc ttatgacagc aagaactgtg    11100
tatgatgatg gtgctaggag agtgtggaca cttatgaatg tcttgacact cgtttataaa    11160
gtttattatg gtaatgcttt agatcaagcc atttccatgt gggctcttat aatctctgtt    11220
acttctaact actcaggtgt agttacaact gtcatgtttt tggccagagg tattgttttt    11280
atgtgtgttg agtattgccc tattttcttc ataactggta atacacttca gtgtataatg    11340
ctagtttatt gtttcttagg ctattttttgt acttgttact ttggcctctt ttgtttactc    11400
aaccgctact ttagactgac tcttggtgtt tatgattact tagtttctac acaggagttt    11460
agatatatga attcacaggg actactccca cccaagaata gcatagatgc cttcaaactc    11520
aacattaaat tgttgggtgt tggtggcaaa ccttgtatca aagtagccac tgtacagtct    11580
aaaatgtcag atgtaaagtg cacatcagta gtcttactct cagttttgca acaactcaga    11640
gtagaatcat catctaaatt gtgggctcaa tgtgtccagt tacacaatga cattctctta    11700
gctaaagata ctactgaagc ctttgaaaaa atggtttcac tactttctgt tttgctttcc    11760
atgcagggtg ctgtagacat aaacaagctt tgtgaagaaa tgctggacaa cagggcaacc    11820
ttacaagcta tagcctcaga gtttagttcc cttccatcat atgcagcttt tgctactgct    11880
caagaagctt atgagcaggc tgttgctaat ggtgattctg aagttgttct taaaaagttg    11940
aagaagtctt tgaatgtggc taaatctgaa tttgaccgtg atgcagccat gcaacgtaag    12000
ttggaaaaga tggctgatca agctatgacc caaatgtata aacaggctag atctgaggac    12060
aagagggcaa aagttactag tgctatgcag acaatgcttt tcactatgct tagaaagttg    12120
gataatgatg cactcaacaa cattatcaac aatgcaagag atggttgtgt tcccttgaac    12180
ataatacctc ttacaacagc agccaaacta atggttgtca taccagacta taacacatat    12240
aaaaatacgt gtgatggtac aacatttact tatgcatcag cattgtggga aatccaacag    12300
gttgtagatg cagatagtaa aattgttcaa cttagtgaaa ttagtatgga caattcacct    12360
aatttagcat ggcctcttat tgtaacagct ttaaggggcca attctgctgt caaattacag    12420
aataatgagc ttagtcctgt tgcactacga cagatgtctt gtgctgccgg tactacacaa    12480
actgcttgca ctgatgacaa tgcgttagct tactacaaca caacaaaggg aggtaggttt    12540
gtacttgcac tgttatccga tttacaggat ttgaaatggg ctagattccc taagagtgat    12600
ggaactggta ctatctatac agaactggaa ccaccttgta ggtttgttac agacacacct    12660
aaaggtccta aagtgaagta tttatacttt attaaaggat taaacaacct aaatagaggt    12720
atggtacttg gtagtttagc tgccacagta cgtctacaag ctggtaatgc aacagaagtg    12780
```

-continued

```
cctgccaatt caactgtatt atctttctgt gcttttgctg tagatgctgc taaagcttac   12840
aaagattatc tagctagtgg gggacaacca atcactaatt gtgttaagat gttgtgtaca   12900
cacactggta ctggtcaggc aataacagtt acaccggaag ccaatatgga tcaagaatcc   12960
tttggtggtg catcgtgttg tctgtactgc cgttgccaca tagatcatcc aaatcctaaa   13020
ggattttgtg acttaaaagg taagtatgta caaataccta caacttgtgc taatgaccct   13080 gtgggttta cacttaaaaa cacagtctgt accgtctgcg gtatgtggaa aggttatggc   13140
tgtagttgtg atcaactccg cgaacccatg cttcagtcag ctgatgcaca atcgttttta   13200
aaccgggttt gcggtgtaag tgcagcccgt cttacaccgt gcggcacagg cactagtact   13260
gatgtcgtat acagggcttt tgacatctac aatgataaag tagctggttt tgctaaattc   13320
ctaaaaacta attgttgtcg cttccaagaa aaggacgaag atgacaattt aattgattct   13380
tactttgtag ttaagagaca cactttctct aactaccaac atgaagaaac aatttataat   13440
ttacttaagg attgtccagc tgttgctaaa catgacttct ttaagtttag aatagacggt   13500
gacatggtac cacatatatc acgtcaacgt cttactaaat acacaatggc agacctcgtc   13560
tatgctttaa ggcattttga tgaaggtaat tgtgacacat aaaagaaat acttgtcaca   13620 tacaattgtt gtgatgatga ttatttcaat aaaaaggact ggtatgattt tgtagaaaac   13680
ccagatatat tacgcgtata cgccaactta ggtgaacgtg tacgccaagc tttgttaaaa   13740
acagtacaat tctgtgatgc catgcgaaat gctggtattg ttggtgtact gacattagat   13800
aatcaagatc tcaatggtaa ctggtatgat ttcggtgatt tcatacaaac cacgccaggt   13860
agtggagttc ctgttgtaga ttcttattat tcattgttaa tgcctatatt aaccttgacc   13920
agggctttaa ctgcagagtc acatgttgac actgacttaa caaagcctta cattaagtgg   13980
gatttgttaa aatatgactt cacggaagag aggttaaaac tctttgaccg ttattttaaa   14040
tattgggatc agacatacca cccaaattgt gttaactgtt tggatgacag atgcattctg   14100
cattgtgcaa actttaatgt tttattctct acagtgttcc cacctacaag ttttggacca   14160
ctagtgagaa aaatatttgt tgatggtgtt ccatttgtag tttcaactgg ataccacttc   14220
agagagctag gtgttgtaca taatcaggat gtaaacttac atagctctag acttagtttt   14280
aaggaattac ttgtgtatgc tgctgaccct gctatgcacg ctgcttctgg taatctatta   14340
ctagataaac gcactacgtg cttttcagta gctgcactta ctaacaatgt tgctttttcaa   14400 actgtcaaac ccggtaattt taacaaagac ttctatgact ttgctgtgtc taagggtttc   14460
tttaaggaag gaagttctgt tgaattaaaa cacttcttct ttgctcagga tggtaatgct   14520
gctatcagcg attatgacta ctatcgttat aatctaccaa caatgtgtga tatcagacaa   14580
ctactatttg tagttgaagt tgttgataag tactttgatt gttacgatgg tggctgtatt   14640
aatgctaacc aagtcatcgt caacaaccta gacaaatcag ctggttttcc atttaataaa   14700
tggggtaagg ctagacttta ttatgattca atgagttatg aggatcaaga tgcactttttc   14760 gcatatacaa aacgtaatgt catccctact ataactcaaa tgaatcttaa gtatgccatt   14820
agtgcaaaga atagagctcg caccgtagct ggtgtctcta tctgtagtac tatgaccaat   14880
agacagtttc atcaaaaatt attgaaatca atagccgcca ctagaggagc tactgtagta   14940
attggaacaa gcaaattcta tggtggttgg cacaacatgt taaaaactgt ttatagtgat   15000
gtagaaaacc ctcacctttat gggttgggat tatcctaaat gtgatagagc catgcctaac   15060
atgcttagaa ttatggcctc acttgttctt gctcgcaaac atacaacgtg ttgtagcttg   15120
tcacaccgtt tctatagatt agctaatgag tgtgctcaag tattgagtga aatggtcatg   15180
```

-continued

```
tgtggcggtt cactatatgt taaaccaggt ggaacctcat caggagatgc cacaactgct   15240
tatgctaata gtgttttttaa catttgtcaa gctgtcacgg ccaatgttaa tgcacttttta  15300 tctactgatg gtaacaaaat tgccgataag tatgtccgca atttacaaca cagactttat   15360
gagtgtctct atagaaatag agatgttgac acagactttg tgaatgagtt ttacgcatat   15420
ttgcgtaaac atttctcaat gatgatactc tctgacgatg ctgttgtgtg tttcaatagc   15480
acttatgcat ctcaaggtct agtggctagc ataaagaact ttaagtcagt tctttattat   15540
caaaacaatg tttttatgtc tgaagcaaaa tgttggactg agactgacct tactaaagga   15600
cctcatgaat tttgctctca acatacaatg ctagttaaac agggtgatga ttatgtgtac   15660
cttccttacc cagatccatc aagaatccta ggggccggct gttttgtaga tgatatcgta   15720
aaaacagatg gtacacttat gattgaacgg ttcgtgtctt tagctataga tgcttaccca   15780
cttactaaac atcctaatca ggagtatgct gatgtctttc atttgtactt acaatacata   15840
agaaagctac atgatgagtt aacaggacac atgttagaca tgtattctgt tatgcttact   15900
aatgataaca cttcaaggta ttgggaacct gagtttttatg aggctatgta cacaccgcat   15960
acagtcttac aggctgttgg ggcttgtgtt ctttgcaatt cacagacttc attaagatgt   16020
ggtgcttgca tacgtagacc attcttatgt tgtaaatgct gttacgacca tgtcatatca   16080
acatcacata aattagtctt gtctgttaat ccgtatgttt gcaatgctcc aggttgtgat   16140
gtcacagatg tgactcaact ttacttagga ggtatgagct attattgtaa atcacataaa   16200
ccacccatta gttttccatt gtgtgctaat ggacaagttt ttggtttata taaaaataca   16260
tgtgttggta gcgataatgt tactgacttt aatgcaattg caacatgtga ctggacaaat   16320
gctggtgatt acatttttagc taacaccttgt actgaaagac tcaagctttt tgcagcagaa   16380
acgctcaaag ctactgagga gacatttaaa ctgtcttatg gtattgctac tgtacgtgaa   16440
gtgctgtctg acagagaatt acatctttca tgggaagttg gtaaacctag accaccactt   16500
aaccgaaatt atgtctttac tggttatcgt gtaactaaaa acagtaaagt acaaatagga   16560
gagtacacct ttgaaaaagg tgactatggt gatgctgttg tttaccgagg tacaacaact   16620
tacaaattaa atgttggtga ttattttgtg ctgacatcac atacagtaat gccattaagt   16680
gcacctacac tagtgccaca agagcactat gttagaatta ctggcttata cccaacactc   16740
aatatctcag atgagttttc tagcaatgtt gcaaattatc aaaaggttgg tatgcaaaag   16800
tattctacac tccagggacc acctggtact ggtaagagtc attttgctat tggcctagct   16860
ctctactacc cttctgctcg catagtgtat acagcttgct ctcatgccgc tgttgatgca   16920
ctatgtgaga aggcattaaa atatttgcct atagataaat gtagtagaat tatacctgca   16980
cgtgctcgtg tagagtgttt tgataaattc aaagtgaatt caacattaga acagtatgtc   17040
ttttgtactg taaatgcatt gcctgagacg acagcagata tagttgtctt tgatgaaatt   17100
tcaatggcca caaattatga tttgagtgtt gtcaatgcca gattacgtgc taagcactat   17160
gtgtacattg gcgaccctgc tcaattacct gcaccacgca cattgctaac taagggcaca   17220
ctagaaccag aatatttcaa ttcagtgtgt agacttatga aaactatagg tccagacatg   17280
ttcctcggaa cttgtcggcg ttgtcctgct gaaattgttg acactgtgag tgctttggtt   17340
tatgataata agcttaaagc acataaagac aaatcagctc aatgctttaa aatgtttttat   17400 aagggtgtta tcacgcatga tgtttcatct gcaattaaca ggccacaaat aggcgtggta   17460
agagaattcc ttacacgtaa ccctgcttgg agaaaagctg tctttatttc accttataat   17520
```

-continued

```
tcacagaatg ctgtagcctc aaagattttg ggactaccaa ctcaaactgt tgattcatca   17580
cagggctcag aatatgacta tgtcatattc actcaaacca ctgaaacagc tcactcttgt   17640
aatgtaaaca gatttaatgt tgctattacc agagcaaaag taggcatact ttgcataatg   17700
tctgatagag acctttatga caagttgcaa tttacaagtc ttgaaattcc acgtaggaat   17760
gtggcaactt tacaagctga aaatgtaaca ggactcttta aagattgtag taaggtaatc   17820
actgggttac atcctacaca ggcacctaca cacctcagtg ttgacactaa attcaaaact   17880
gaaggtttat gtgttgacat acctggcata cctaaggaca tgacctatag aagactcatc   17940
tctatgatgg gtttttaaaat gaattatcaa gttaatggtt accctaacat gtttatcacc   18000
cgcgaagaag ctataagaca tgtacgtgca tggattggct tcgatgtcga ggggtgtcat   18060
gctactagag aagctgttgg taccaattta cctttacagc taggtttttc tacaggtgtt   18120
aacctagttg ctgtacctac aggttatgtt gatacaccta ataatacaga ttttttccaga   18180 gttagtgcta aaccaccgcc tggagatcaa tttaaacacc tcataccact tatgtacaaa   18240
ggacttcctt ggaatgtagt gcgtataaag attgtacaaa tgttaagtga cacacttaaa   18300
aatctctctg acagagtcgt atttgtctta tgggcacatg gctttgagtt gacatctatg   18360
aagtattttg tgaaaatagg acctgagcgc acctgttgtc tatgtgatag acgtgccaca   18420
tgcttttcca ctgcttcaga cacttatgcc tgttggcatc attctattgg atttgattac   18480
gtctataatc cgtttatgat tgatgttcaa caatgggggt ttacaggtaa cctacaaagc   18540
aaccatgatc tgtattgtca agtccatggt aatgcacatg tagctagttg tgatgcaatc   18600
atgactaggt gtctagctgt ccacgagtgc tttgttaagc gtgttgactg gactattgaa   18660
tatcctataa ttggtgatga actgaagatt aatgcggctt gtagaaaggt tcaacacatg   18720
gttgttaaag ctgcattatt agcagacaaa ttcccagttc ttcacgacat tggtaaccct   18780
aaagctatta gtgtgtacc tcaagctgat gtagaatgga gttctatga tgcacagcct   18840 tgtagtgaca aagcttataa aatagaagaa ttattctatt cttatgccac acattctgac   18900
aaattcacag atggtgtatg cctattttgg aattgcaatg tcgatagata tcctgctaat   18960
tccattgttt gtagatttga cactagagtg ctatctaacc ttaacttgcc tggttgtgat   19020
ggtggcagtt tgtatgtaaa taaacatgca ttccacacac cagctttttga taaaagtgct   19080 tttgttaatt taaaacaatt accattttttc tattactctg acagtccatg tgagtctcat   19140
ggaaaacaag tagtgtcaga tatagattat gtaccactaa agtctgctac gtgtataaca   19200
cgttgcaatt taggtggtgc tgtctgtaga catcatgcta atgagtacag attgtatctc   19260
gatgcttata acatgatgat ctcagctggc tttagcttgt gggtttacaa acaatttgat   19320
acttataacc tctggaacac tttttacaaga cttcagagtt tagaaaatgt ggctttttaat   19380 gttgtaaata agggacactt tgatggacaa caggtgaag taccagtttc tatcattaat   19440
aacactgttt acacaaaagt tgatggtgtt gatgtagaat tgtttgaaaa taaaacaaca   19500
ttacctgtta atgtagcatt tgagctttgg gctaagcgca acattaaacc agtaccagag   19560
gtgaaaatac tcaataattt gggtgtggac attgctgcta atactgtgat ctgggactac   19620
aaaagagatg ctccagcaca tatatctact attggtgttt gttctatgac tgacatagcc   19680
aagaaaccaa ctgaaacgat ttgtgcacca ctcactgtct tttttgatgg tagagttgat   19740
ggtcaagtag acttatttag aaatgcccgt aatggtgttc ttattacaga aggtagtgtt   19800
aaaggtttac aaccatctgt aggtcccaaa caagctagtc ttaatggagt cacattaatt   19860
ggagaagccg taaaaacaca gttcaattat tataagaaag ttgatggtgt tgtccaacaa   19920
```

-continued

```
ttacctgaaa cttactttac tcagagtaga aatttacaag aatttaaacc caggagtcaa    19980
atggaaattg atttcttaga attagctatg gatgaattca ttgaacggta taaattagaa    20040
ggctatgcct tcgaacatat cgtttatgga gattttagtc atagtcagtt aggtggttta    20100
catctactga ttggactagc taaacgtttt aaggaatcac cttttgaatt agaagatttt    20160
attcctatgg acagtacagt taaaaactat ttcataacag atgcgcaaac aggttcatct    20220
aagtgtgtgt gttctgttat tgatttatta cttgatgatt ttgttgaaat aataaaatcc    20280
caagatttat ctgtagtttc taaggttgtc aaagtgacta ttgactatac agaaatttca    20340
tttatgcttt ggtgtaaaga tggccatgta gaaacatttt acccaaaatt acaatctagt    20400
caagcgtggc aaccgggtgt tgctatgcct aatctttaca aaatgcaaag aatgctatta    20460
gaaaagtgtg accttcaaaa ttatggtgat agtgcaacat tacctaaagg cataatgatg    20520
aatgtcgcaa aatatactca actgtgtcaa tatttaaaca cattaacatt agctgtaccc    20580
tataatatga gagttataca ttttggtgct ggttctgata aaggagttgc accaggtaca    20640 gctgtttttaa gacagtggtt gcctacgggt acgctgcttg tcgattcaga tcttaatgac    20700
tttgtctctg atgcagattc aactttgatt ggtgattgtg caactgtaca tacagctaat    20760
aaatgggatc tcattattag tgatatgtac gaccctaaga ctaaaaatgt tacaaaagaa    20820
aatgactcta agagggtttt tttcacttac atttgtgggt ttatacaaca aaagctagct    20880
cttggaggtt ccgtggctat aaagataaca gaacattctt ggaatgctga tctttataag    20940
ctcatgggac acttcgcatg gtggacagcc tttgttacta atgtgaatgc gtcatcatct    21000
gaagcatttt taattggatg taattatctt ggcaaaccac gcgaacaaat agatggttat    21060
gtcatgcatg caaattacat attttggagg aatacaaatc caattcagtt gtcttcctat    21120
tctttatttg acatgagtaa atttcccctt aaattaaggg gtactgctgt tatgtcttta    21180
aaagaaggtc aaatcaatga tatgattta tctcttctta gtaaaggtag acttataatt    21240
agagaaaaca acagagttgt tatttctagt gatgttcttg ttaacaacta a            21291
```

<210> SEQ ID NO 8
<211> LENGTH: 1260
<212> TYPE: DNA
<213> ORGANISM: Severe Acute Respiratory Syndrome Coronavirus 2

<400> SEQUENCE: 8

```
atgtctgata atggacccca aaatcagcga aatgcacccc gcattacgtt tggtggaccc       60
tcagattcaa ctggcagtaa ccagaatgga gaacgcagtg gggcgcgatc aaaacaacgt      120
cggccccaag gtttacccaa taatactgcg tcttggttca ccgctctcac tcaacatggc      180
aaggaagacc ttaaattccc tcgaggacaa ggcgttccaa ttaacaccaa tagcagtcca      240
gatgaccaaa ttggctacta ccgaagagct accagacgaa ttcgtggtgg tgacggtaaa      300
atgaaagatc tcagtccaag atggtatttc tactacctag gaactgggcc agaagctgga      360
cttccctatg gtgctaacaa agacggcatc atatgggttg caactgaggg agccttgaat      420
acaccaaaag atcacattgg cacccgcaat cctgctaaca atgctgcaat cgtgctacaa      480
cttcctcaag gaacaacatt gccaaaaggc ttctacgcag aagggagcag aggcggcagt      540
caagcctctt ctcgttcctc atcacgtagt cgcaacagtt caagaaattc aactccaggc      600
agcagtaggg gaacttctcc tgctagaatg gctggcaatg gcggtgatgc tgctcttgct      660
ttgctgctgc ttgacagatt gaaccagctt gagagcaaaa tgtctggtaa aggccaacaa      720
```

```
caacaaggcc aaactgtcac taagaaatct gctgctgagg cttctaagaa gcctcggcaa    780
aaacgtactg ccactaaagc atacaatgta acacaagctt tcggcagacg tggtccagaa    840
caaacccaag gaaattttgg ggaccaggaa ctaatcagac aaggaactga ttacaaacat    900
tggccgcaaa ttgcacaatt tgcccccagc gcttcagcgt tcttcggaat gtcgcgcatt    960
ggcatggaag tcacaccttc gggaacgtgg ttgacctaca caggtgccat caaattggat   1020
gacaaagatc caaatttcaa agatcaagtc attttgctga ataagcatat tgacgcatac   1080
aaaacattcc caccaacaga gcctaaaaag gacaaaaaga agaaggctga tgaaactcaa   1140
gccttaccgc agagacagaa gaaacagcaa actgtgactc ttcttcctgc tgcagatttg   1200
gatgatttct ccaaacaatt gcaacaatcc atgagcagtg ctgactcaac tcaggcctaa   1260
```

MOLECULAR DETECTION OF NOVEL CORONAVIRUSES

CROSS-REFERENCE TO RELATED APPLICATIONS

This application claims priority to and the benefit of U.S. Application No. 63/143,930, filed on Jan. 31, 2021, which is incorporated herein by reference in its entirety.

STATEMENT REGARDING FEDERALLY SPONSORED RESEARCH

This invention was made with government support under HHSN272201400006C awarded by the National Institutes of Health. The government has certain rights in the invention.

REFERENCE TO SEQUENCE LISTING

The Sequence Listing submitted Dec. 8, 2021, as a text file named "UHK_01011_ST25.txt," created on Dec. 2, 2021, and having a size of 31,463 bytes is hereby incorporated by reference pursuant to 37 C.F.R. § 1.52(e)(5).

FIELD OF THE INVENTION

The invention is generally directed to the identification and quantification of coronavirus RNA within a sample, specifically using a Reverse-Transcription Quantitative Polymerase Chain Reaction (RT-qPCR) assay.

BACKGROUND OF THE INVENTION

The Severe Acute Respiratory Syndrome Coronavirus 2 (SARS-CoV-2) is a highly transmissible and pathogenic coronavirus that causes acute respiratory disease in humans known as Coronavirus disease 2019 (COVID-19). SARS-CoV-2 spread rapidly across the world from its discovery in late 2019 to early 2020, prompting The World Health Organization (WHO) to declare a global pandemic in mid-March 2020 (Hu, B., Guo, H., Zhou, P. et al., Nat Rev Microbiol 19, 141-154 (2021)). A little more than one year after the first case of SARS-CoV-2 was reported, over 85.6 million infections had been confirmed worldwide, and SARS-CoV-2 had been associated with more than 1.8 million deaths. The United States alone reported more than 21 million cases of COVID-19, and over 360,000 deaths associated with SARS-CoV-2 by early January 2021 (WHO Coronavirus disease (COVID-19) Weekly Epidemiological Update and Weekly Operational Update; website who.int/emergencies/diseases/novel-coronavirus-2019/situation-reports/).

COVID-19 in humans is characterized by a wide range of symptoms, ranging from very mild or asymptomatic cases to severe and sometimes fatal respiratory diseases. Symptoms may appear at any point up to 14 days following exposure.

The rapid human-to-human transmission, together with the extensive incubation period highlight the necessity for early identification of infected patients. The non-specific nature of symptoms associated with COVID-19, together with the extremely high demand for diagnostic tests also highlight the need for rapid and reliable molecular systems to identify SARS-CoV-2 in clinical samples.

Quantification of viral infectious units is traditionally measured by methods based on forming plaques in semisolid media (PFU) or endpoint dilution of a virus-containing solution (TCID50), methods that are laborious, time-consuming and take on average 3-7 days to carry out (Jonsson et al., *Microbiol Immunol* 2009; 53: 149-154).

Therefore, it is an object of the invention to provide a compositions and methods for the rapid and reproducible detection of SARS-CoV-2 in clinical samples.

It is another object to provide compositions and methods which accurately quantify and distinguish between viruses of the subgenus Sarbecovirus with different genetic backgrounds.

It is a further object to provide compositions and methods for monitoring and recording the infectivity of SARS-CoV-2 in clinical samples associated with development and progression of COVID-19 in patients.

SUMMARY OF THE INVENTION

A real-time Reverse-Transcription Quantitative Polymerase Chain Reaction (RT-qPCR technique for detection of two different regions (ORF1b and N) of the SARS-CoV-2 viral genome has been developed. Compositions for rapid detection of COVID-19 in human samples using a single RT-qPCR and methods thereof are provided. The compositions include nucleic acids for detection of SARS-CoV-2 virus N gene and/or SARS-CoV-2 virus ORF1b gene.

In some forms, the composition for the detection of SARS-CoV-2 virus N gene can include PCR primers for amplifying a segment of the SARS-CoV-2 virus N gene comprising nucleotides corresponding to nucleotides 905-923 of SEQ ID NO:8. In some forms, the composition for the detection of SARS-CoV-2 virus N gene can include PCR primers for amplifying a segment of the SARS-CoV-2 virus N gene comprising nucleotides corresponding to nucleotides 894-962 of SEQ ID NO:8. In some forms, the composition for the detection of SARS-CoV-2 virus N gene can include PCR primers for amplifying a segment of the SARS-CoV-2 virus N gene comprising nucleotides corresponding to nucleotides 872-981 of SEQ ID NO:8.

In some forms, the composition for the detection of SARS-CoV-2 virus N gene can include (i) a nucleic acid having the sequence of SEQ ID NO:4, or a nucleic acid sequence having at least 90%, 95%, 96%, 97%, 98%, or 99% sequence identity to SEQ ID NO:4, and (ii) a nucleic acid having the sequence of SEQ ID NO:5, or a nucleic acid sequence having at least 90%, 95%, 96%, 97%, 98%, or 99% sequence identity to SEQ ID NO:5. In some forms, the composition for the detection of SARS-CoV-2 virus N gene further include a nucleic acid probe having one or more fluorescent reporters, one or more quenchers, or a combination thereof, wherein the probe is configured to specifically bind to a nucleic acid sequence within SEQ ID NO:8. In some forms, the probe is configured to specifically bind to a segment of the SARS-CoV-2 virus N gene comprising nucleotides corresponding to nucleotides 905-923 of SEQ ID NO:8. In some forms, the probe is configured to specifically bind to a segment of the SARS-CoV-2 virus N gene comprising nucleotides corresponding to nucleotides 894-962 of SEQ ID NO:8. In some forms, the probe is configured to specifically bind to a segment of the SARS-CoV-2 virus N gene comprising nucleotides corresponding to nucleotides 872-981 of SEQ ID NO:8.

In a preferred form, the nucleic acid probe configured to specifically bind to a nucleic acid sequence within SEQ ID NO:8 has a nucleic acid sequence of SEQ ID NO:6, or a nucleic acid sequence having at least 90%, 95%, 96%, 97%, 98%, or 99% sequence identity to SEQ ID NO:6.

In some forms, the composition for the detection of SARS-CoV-2 virus ORF1b gene can include PCR primers for amplifying a segment of the SARS-CoV-2 virus ORF1b gene comprising nucleotides corresponding to nucleotides 18547-18565 of SEQ ID NO:7. In some forms, the composition for the detection of SARS-CoV-2 virus ORF1b gene can include PCR primers for amplifying a segment of the SARS-CoV-2 virus ORF1b gene comprising nucleotides corresponding to nucleotides 18536-18604 of SEQ ID NO:7. In some forms, the composition for the detection of SARS-CoV-2 virus ORF1b gene can include PCR primers for amplifying a segment of the SARS-CoV-2 virus ORF1b gene comprising nucleotides corresponding to nucleotides 18514-18645 of SEQ ID NO:7.

In some forms, the composition for the detection of SARS-CoV-2 virus ORF1b gene can include (i) a nucleic acid having the sequence of SEQ ID NO:1, or a nucleic acid sequence having at least 90%, 95%, 96%, 97%, 98%, or 99% sequence identity to SEQ ID NO:1, and (ii) a nucleic acid having the sequence of SEQ ID NO:2, or a nucleic acid sequence having at least 90%, 95%, 96%, 97%, 98%, or 99% sequence identity to SEQ ID NO:2. In some forms, the composition for the detection of SARS-CoV-2 virus ORF1b gene further include a nucleic acid probe having one or more fluorescent reporters, one or more quenchers, or a combination thereof, wherein the probe is configured to specifically bind to a nucleic acid sequence within SEQ ID NO:7. In some forms, the probe is configured to specifically bind to a segment of the SARS-CoV-2 virus ORF1b gene comprising nucleotides corresponding to nucleotides 18547-18565 of SEQ ID NO:7. In some forms, the probe is configured to specifically bind to a segment of the SARS-CoV-2 virus ORF1b gene comprising nucleotides corresponding to nucleotides 18536-18604 of SEQ ID NO:7. In some forms, the probe is configured to specifically bind to a segment of the SARS-CoV-2 virus ORF1b gene comprising nucleotides corresponding to nucleotides 18514-18645 of SEQ ID NO:7.

In a preferred form, the nucleic acid probe configured to specifically bind to a nucleic acid sequence within SEQ ID NO:7 has a nucleic acid sequence of SEQ ID NO:3, or a nucleic acid sequence having at least 90%, 95%, 96%, 97%, 98%, or 99% sequence identity to SEQ ID NO:3.

The compositions for RT-qPCR further include one or more of a phosphate buffer, a Tris buffer, a potassium salt, a sodium salt, a magnesium salt, an ammonium salt, dATP, dCTP, dGTP, and dTTP, a reverse transcriptase enzyme, and a DNA polymerase enzyme. In some forms, the salt is selected from the group consisting of KCl, NaCl, $MgCl_2$, $MgSO_4$, $(NH_4)_2SO_4$. In some forms, the DNA polymerase is Taq polymerase.

Methods for detecting and quantifying the presence of the SARS-CoV-2 virus with high sensitivity in a biological sample have been established. These methods are useful in the diagnosis, prognosis, epidemiology, and monitoring of progression and treatment of COVID-19. The methods detect viral target RNA based on as few as 10 copies of target RNA per sample.

Typically, the methods for detecting and quantifying the presence of the SARS-CoV-2 include one or more steps to detect and quantify the target RNA within an input sample. In some forms, the target RNA codes for the N protein of the SARS-CoV-2 virus. In some forms, the target RNA codes for the ORF1 protein of the SARS-CoV-2 virus. In particular forms, the methods include one or more steps to detect and label the presence of RNA coding for the N protein of the SARS-CoV-2 virus, as well as RNA coding for the ORF1 protein of the SARS-CoV-2 virus within the same sample, or from within different samples from the same patient. In some forms, the methods include contacting the input sample with the disclosed compositions for the detection of SARS-CoV-2 virus N gene under conditions sufficient for amplification of the N gene of SARS-CoV-2, wherein detection of the SARS-CoV-2 N gene amplification product indicates the presence of SARS-CoV-2 in the input sample. In some forms, the input sample includes purified nucleic acids such as viral RNA. Thus, in some forms, the method includes a step of extracting nucleic acids from a biological sample to create the input sample. Typically, the biological sample is a bodily fluid of a subject, the bodily fluid selected from the group consisting of mucus, sputum (processed or unprocessed), bronchial alveolar lavage (BAL), bronchial wash (BW), bodily fluids, cerebrospinal fluid (CSF), urine, tissue (e.g., biopsy material), rectal swab, nasopharyngeal aspirate, nasopharyngeal swab, throat swab, feces, plasma, serum, and whole blood. Thus, in some forms, the method includes a step of obtaining the biological sample from the subject. In some forms, the subject is a subject who has one or more symptoms of COVID-19, an asymptomatic subject who is at increased risk of being infected with SARS-CoV-2 virus, a subject who has received a vaccine against infection with SARS-CoV-2 virus, and a deceased subject. The typical input sample contains 10 or more copies of the SARS-CoV-2 N gene. In preferred forms, the methods further include b) contacting the input sample with the disclosed composition for the detection of SARS-CoV-2 virus ORF1b gene under conditions sufficient for amplification of the ORF1b gene of SARS-CoV-2, wherein detection the SARS-CoV-2 ORF1b gene amplification product indicates the presence of SARS-CoV-2 in the input sample. The typical input sample contains 10 or more copies of the SARS-CoV-2 ORF1b gene.

In some forms, the methods include steps for quantifying and/or recording the number of copies of viral target RNAs within the sample. In some forms, the methods include one or more steps to record the number of copies of viral target RNAs within a sample together with one or more additional pieces of datum relating to the sample or patient. For example, in some forms, the methods record the number of copies of viral target RNAs within a sample together with one or more time points, such as the time post-exposure to the SARS-CoV-2 virus, and/or the time post onset of one or more symptoms of COVID-19. In some forms, the methods include combining the data from two or more assays to form one or more databases. For example, in some forms, the methods record the number of copies of viral target RNAs within a sample together with one or more time points, such as the time post-exposure to the SARS-CoV-2 virus, and/or the time post onset of one or more symptoms of COVID-19 for two or more patients. In some forms, the methods include combining the data from two or more assays with one or more pieces of data relating to the patient, such as the patient age, patient genetic background, disease symptoms, or other physiological or pathological information.

Typically, the methods effectively identify the presence of the SARS-CoV-2 virus within a sample having a minimum number of copies of the target viral RNA. In preferred forms, the minimum number of copies of the target viral RNA required for identification of the SARS-CoV-2 virus within a sample is less than 10, for example, one two, three, four, five, six, seven, eight, nine, ten, or more than 10, such as 11, 12, 13, 14, 15, 16, 17, 18, 19, or 20 or more, 30, 40, 50, 60, 70, 80 or 100 or more.

In some forms, the methods detect an amount of virus within a sample from a patient that is present prior to the onset of symptoms in the patient. In some forms, the methods detect an amount of virus within a sample from a patient that is present within one, two, three, four, five, six, seven, eight, nine, or ten hours or days following the initial exposure of the patient to the virus.

In some forms, the methods include the step of determining the sequence of one or more of the genes of a SARS-CoV-2 virus within a sample identified as containing the SARS-CoV-2. In some forms, the methods include one or more steps for recording the sequence data from one or more genes of one or more SARS-CoV-2 viruses within one or more databases, optionally together with one or more pieces of data relating the same or different samples.

In some forms, the methods include screening one or more positive and/or negative controls. Exemplary positive controls include one or more RNA sequences encoding one or more of the target viral RNAs. Exemplary positive control RNA sequences include plasmids, or as cells expressing SARS-CoV-2 viruses, or DNA plasmids containing the target sequences. Exemplary negative controls include one or more RNA sequences specific for one or more distinct human respiratory pathogen. Exemplary distinct human respiratory pathogens include human coronaviruses 229E, OC43, and MERS, camel coronavirus HKU23, human influenza A viruses H1N1, H3N2, H5N1, and H7N9 subtypes, avian influenza H1, H4, H6, and H9 subtypes, influenza B virus Yamagata and Victoria lineages, adenovirus, enterovirus, human parainfluenza virus (PIV1, 2, 3 and 4), respiratory syncytial virus, human metapneumovirus, rhinovirus and human bocavirus, and RNA extracted from sputum samples from patients without respiratory viral infections.

In some forms, when the methods do not identify the presence of SARS-CoV-2 virus with the sample, the methods include one or more additional RT-qPCR steps to identify the presence of one of more additional human respiratory pathogens within the same sample. Exemplary additional human respiratory pathogens include one or more of the pathogens included as a negative control.

In some forms, the methods include treating a patient identified as being infected with the SARS-CoV-2 virus. In some forms, treatment is initiated prior to the onset of symptoms in the patient.

BRIEF DESCRIPTION OF THE DRAWINGS

FIG. 1A shows the nucleic acid sequence of the SARS-CoV-2 ("2019-nCoV") viral gene ORF-1b amplicon (upper sequence), aligned with that from the SARS-CoV Urbani strain isolated from patients with SARS respiratory disease in Asia during the 2003 SARS epidemic ("SARS-CoV (Urbani starin)") (lower sequence). FIG. 1B shows the nucleic acid sequence of the SARS-CoV-2 viral gene N (upper sequence), with that from the SARS-CoV (Urbani strain) (lower sequence). Arrows indicate the regions targeted by the studied primers. Nucleic acids are represented in single letter code in the upper sequences. Sequence alignment is depicted in the lower sequence, with a dot representing a matching nucleotide, and mis-matched nucleotides represented in single letter code.

DETAILED DESCRIPTION OF THE INVENTION

I. Definitions

Figure 1A:
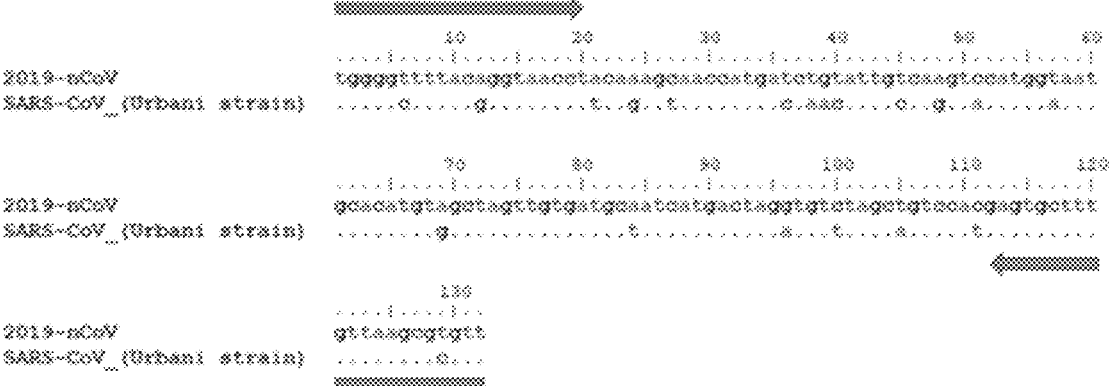
FIGS. 1A-1B show sequence alignments for the targeted regions of viral RNA.

The terms "SARS-CoV-2" and "Severe Acute Respiratory Syndrome Coronavirus 2" refer to the pathogenic coronavirus strains of the subgenus Sarbecovirus which are directly descended from the coronavirus of zoonotic origin which emerged in Asia in late 2019, and which are the causative agents of pandemic Coronavirus disease 2019 (COVID-19) in humans. An exemplary nucleic acid sequence for a SARS-CoV-2 virus is deposited in GenBank as accession No: MN908947.3.

The term "ORF1a/ORF1b" refers to the gene located at the 5' region of the SARS-CoV-2 coronavirus RNA genome which encodes two polyproteins (encoded by ORF1a and ORF1b). ORF1ab is the longest ORF occupying ⅔ of the entire genome. A representative ORF1b gene from the SARS-CoV-2 coronavirus is deposited in GenBank as accession No: MN908947.3, which has the nucleic acid sequence of SEQ ID NO:7.

The term "N gene" refers to the gene which encodes the nucleocapsid protein, located at the 3' region of the SARS-CoV-2 coronavirus RNA genome encoding a polyprotein. A representative N gene from the SARS-CoV-2 coronavirus is deposited in GenBank as accession No: MN908947.3, which has the nucleic acid sequence of SEQ ID NO:8.

As used herein, the term "nucleic acid molecule" is used broadly to mean any polymer of two or more nucleotides, which are linked by a covalent bond such as a phosphodiester bond, a thioester bond, or any of various other bonds known in the art as useful and effective for linking nucleotides. Such nucleic acid molecules can be linear, circular or supercoiled, and can be single stranded or double stranded, e.g., single stranded or double stranded DNA, RNA or DNA/RNA hybrid. In some forms, nucleic acid molecules are or include nucleic acid analogs that are less susceptible to degradation by nucleases than are DNA and/or RNA.

The terms "targeted gene" or "target nucleic acid" or "target sequence" or "target segment" as used herein refer to a nucleic acid sequence of interest to be detected and/or quantified in the sample to be analyzed. Target nucleic acid may be composed of segments of a genome, a complete gene with or without intergenic sequence, segments or portions of a gene with or without intergenic sequence, or sequence of nucleic acids to which probes or primers are designed to hybridize. Target nucleic acids may include a wild-type sequence(s), a mutation, deletion, insertion or duplication, tandem repeat elements, a gene of interest, a region of a gene of interest or any upstream or downstream region thereof. Target nucleic acids may represent alternative sequences or alleles of a particular gene. Target nucleic acids may be derived from genomic DNA, cDNA, or RNA. In preferred forms, the target sequence refers to a gene or genomic component within a coronavirus, which is targeted by one or more primers designed to selectively bind and amplify the gene during RT-qPCR.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer "buffer" includes pH, ionic strength, cofactors etc.), and at a suitable temperature. One or more of the nucleotides of the primer can be modified for instance by addition of a methyl group, a biotin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, labeled primers, and the like. The term "forward primer" as used herein means a primer that anneals to the anti-sense strand of double-stranded DNA (dsDNA). A "primer" anneals to the sense-strand of dsDNA. Primers are typically at least 10, 15, 18, or 30 nucleotides in length or up to about 100, 110, 125, or 200 nucleotides in length. In some forms, primers are preferably between about 15 to about 60 nucleotides in length, and most preferably between about 25 to about 40 nucleotides in length. In some forms, primers are 15 to 35 nucleotides in length. There is no standard length for optimal hybridization or polymerase chain reaction amplification. An optimal length for a particular primer application may be readily determined in the manner described in H. Erlich, PCR Technology, Principles and Application for DNA Amplification, (1989).

The term "amplification" as used herein refers to increasing the number of copies of a nucleic acid molecule, such as a gene or fragment of a gene, for example at least a portion of the SARS-CoV-2 RNA. The products of an amplification reaction are called amplification products. An example of in vitro amplification is RT-PCR amplification.

The term "conditions sufficient for" as used herein in connection with the disclosed methods, refers to any environment that permits the desired activity, for example, that permits specific binding or hybridization between two nucleic acid molecules or that permits reverse transcription and/or amplification of a nucleic acid. Such an environment may include, but is not limited to, particular incubation conditions (such as time and/or temperature) or presence and/or concentration of particular factors, for example in a solution (such as buffer(s), salt(s), metal ion(s), detergent(s), nucleotide(s), enzyme(s), etc).

The term "contact" as used herein in connection with the disclosed methods refers to placement in direct physical association; for example, in solid and/or liquid form. For example, contacting can occur in vitro with one or more primers and/or probes and a biological sample (such as a sample including nucleic acids) in solution.

As used herein, the term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

As used herein, the term "sensitivity" refers to the ability of a test to correctly identify true positives, i.e., patients infected with SARS-CoV-2. For example, sensitivity can be expressed as a percentage, the proportion of actual positives which are correctly identified as such (e.g., the percentage of test subjects having SARS-CoV-2 correctly identified by the test as having SARS-CoV-2). A test with high sensitivity has a low rate of false negatives, i.e., the cases of SARS-CoV-2 not identified as such. Generally, the disclosed assays and methods have a sensitivity of at least 90%, at least 92%, at least 94%, at least 95%, at least 96%, at least 97%, at least 98%, at least 99%, or at least 100%.

As used herein, the term "specificity" refers to the ability of a test to correctly identify true negatives, i.e., the individuals that have no SARS-CoV-2 infection. For example, specificity can be expressed as a percentage, the proportion of actual negatives which are correctly identified as such (e.g., the percentage of test subjects not having SARS-CoV-2 correctly identified by the test as not having SARS-CoV-2). A test with high specificity has a low rate of false positives, i.e., the cases of individuals not having SARS-CoV-2 but suggested by the test as having SARS-CoV-2. Generally, the disclosed methods have a specificity of at least 90%, at least 92%, at least 94%, at least 95%, at least 96%, at least 97%, at least 98%, at least 99%, or at least 100%.

As used herein, the term "accurate" refers to the ability of a test to provide a result with high sensitivity and high specificity, such as with sensitivity over about 80% and specificity over about 80%, with sensitivity over about 85% and specificity over about 85%, or with sensitivity over about 90% and specificity over about 90%.

As used herein, the term "sample" refers to body fluids, body smears, cell, tissue, organ, or portion thereof that is isolated from a subject. A sample may be a single cell or a plurality of cells. A sample may be a specimen obtained by biopsy (e.g., surgical biopsy).

A sample may be cells from a subject that are or have been placed in or adapted to tissue culture. A sample may be one or more of cells, tissue, serum, plasma, urine, spittle, sputum, and stool. A sample may be one or more of a swab, fluid, blood, plasma, serum, urine, sputum, or exudate. An "input" sample includes RNA obtained from a sample, extracted or purified in a form suitable for effective analysis according to the described methods for RT-qPCR.

As used herein, the terms "subject," "individual" or "patient" refer to a human or a non-human mammal A subject may be a non-human primate, domestic animal, farm animal, or a laboratory animal. For example, the subject may be a dog, cat, goat, horse, pig, mouse, rabbit, or the like. The subject may be a human. The subject may be healthy or suffering from or susceptible to a disease, disorder, or condition. A patient refers to a subject afflicted with a disease or disorder. The term "patient" includes human and veterinary subjects.

A "control" sample or value refers to a sample that serves as a reference, usually a known reference, for comparison to a test sample. For example, a test sample can be taken from a test subject, and a control sample can be taken from a control subject, such as from a known normal (non-disease) individual. A control can also represent an average value gathered from a population of similar individuals, e.g., disease patients or healthy individuals with a similar medical background, same age, weight, etc. One of skill will recognize that controls can be designed for assessment of any number of parameters.

As used herein, the term "symptomatic" refers to a subject with one or more symptoms of SARS-CoV-2 infection detectable by non-invasive methods, such as with one or more of fever, cough, tiredness, joint pain, headache, shortness of breath, etc.

As used herein, the term "asymptomatic" refers to a subject having an absence of one or more symptoms of SARS-CoV-2 infection detectable by non-invasive methods, such as with one or more of fever, cough, tiredness, joint pain, headache, shortness of breath, etc.

As used herein, the term "screening" refers to testing a sample from an individual, or from a population of individuals, with known or unknown status of infection.

The terms "detect," and "identify," in the context of an assay are used interchangeably and refer to the positive identification of a target, such as genetic component of a coronavirus. The identification or detection can be interpreted or assessed according to the mechanism of an assay, and identification or detection can be compared to a control or to a standard level. For example, in a RT-qPCR assay, the extent of detection of a gene or expressed gene product may be quantified as complete (i.e., 100%) or partial (i.e., 1-99.9%) of the expected or calculated level of that in a control. Quantitation can be measured as a % value, e.g., from 1% up to 100%, such as 5%, 10, 25, 50, 75, 80, 85, 90, 95, 99, or 100%. For example, the relative amount of a target gene, or the activity or quantity of one or more expressed gene products can be assessed relative to a control, or relative to another experimental sample. In some forms, the detection or quantitation are compared according to the level of RNAs, or proteins corresponding to the targeted genetic element within a control cell.

The term "pharmaceutically acceptable" or "biocompatible" refers to compositions, polymers, and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions, or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The terms "treating" or "preventing" mean to ameliorate, reduce or otherwise stop a disease, disorder or condition from occurring or progressing in a subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition. Desirable effects of treatment include decreasing the rate of disease progression, ameliorating, or palliating the disease state, and remission or improved prognosis. For example, an individual is successfully "treated" if one or more symptoms associated with a coronavirus infection or associated disease or disorder are mitigated or eliminated, including, but are not limited to, reducing and/or inhibiting rate of viral proliferation/growth, increasing the quality of life of those suffering from the disease, decreasing the dose of medications required to treat the disease, delaying the progression of the disease, and/or prolonging survival of individuals.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other aspects the values may range in value either above or below the stated value in a range of approx. +/−5%; in other aspects the values may range in value either above or below the stated value in a range of approx. +/−2%; in other aspects the values may range in value either above or below the stated value in a range of approx. +/−1%.

II. Compositions

Systems and compositions that can be used to rapidly and reliably identify the presence of SARS-CoV-2 viruses within a sample has been established. The systems employ RT-qPCR with primers designed to recognize two distinct genes having conserved sequences amongst SARS-CoV-2 viruses associated with the COVI-19 pandemic. The systems include one or more sets of nucleic acid primer probes for annealing to viral RNA within a test sample.

Compositions for a one-step, multi-target RT-qPCR-based molecular assay system for detection of SARS-CoV-2 viruses are provided. The assay system overcomes the limitations of lengthy and resource-heavy steps, which are associated with other laboratory-based molecular diagnostic methods. The compositions are particularly effective for the rapid and sensitive detection and quantitation of SARS-CoV-2 viruses within biological samples, such as sputum samples. The systems and compositions identify SARS-CoV-2 viruses within the sample if they possess an N gene and/or ORF1b gene of a specific sequence, and can detect/quantify as few as 10 copies of the viral N gene or ORF1b gene within the sample. The RT-qPCR-based systems employ a pair of target-specific primers labelled with a detectable probe to monitor the reverse-transcription polymerase chain reaction within a mixture including an experimental sample. The RT-qPCR assay is dependent on a highly-sequence specific alignment of the primer probes with template RNA or DNA within the sample, to achieve sequence-specific detection and quantitation in real-time.

A. Viral Targets

The systems and compositions identify viruses, particularly the SARS-CoV-2 viruses, which are coronaviruses of the subgenus Sarbecovirus.

1. Coronaviruses

The coronaviruses (order Nidovirales, family Coronaviridae, and genus Coronavirus) are a diverse group of large, enveloped, positive-stranded RNA viruses that cause respiratory and enteric diseases in humans and other animals (Rota, et al., Science, May 2003, Page 1/10.1126/1085952).

Coronaviruses typically have narrow host and can cause severe disease in many animals, and several viruses, including infectious bronchitis virus, feline infectious peritonitis virus, and transmissible gastroenteritis virus, are significant veterinary pathogens. Human coronaviruses (HCoVs) are found in both group 1 (HCoV-229E) and group 2 (HCoV-0C43) and are historically responsible for ~30% of mild upper respiratory tract illnesses.

At ~30,000 nucleotides, their genome is the largest found in any of the RNA viruses. There are three groups of coronaviruses; groups 1 and 2 contain mammalian viruses, while group 3 contains only avian viruses. Within each group, coronaviruses are classified into distinct species by host range, antigenic relationships, and genomic organization. The genomic organization is typical of coronaviruses, with the characteristic gene order (5'-replicase [rep], spike [S], envelope [E], membrane [M], nucleocapsid [N]-3') and short untranslated regions at both termini. The SARS-CoV rep gene, which comprises approximately two-thirds of the genome, encodes two polyproteins (encoded by ORF1a and ORF1b) that undergo co-translational proteolytic processing. There are four open reading frames (ORFs) downstream of rep that are predicted to encode the structural proteins, S, E, M, and N, which are common to all known coronaviruses.

a. SARS-CoV-2

The systems and compositions identify the SARS-CoV-2 betacoronavirus of the subgenus Sarbecovirus. SARS- CoV-2 viruses share approximately 79% genome sequence identity with the SARS-CoV virus identified in 2003. The genome organization of SARS-CoV-2 viruses is shared with other betacoronaviruses; six functional open reading frames (ORFs) are arranged in order from 5' to 3': replicase (ORF1a/ORF1b), spike (S), envelope (E), membrane (M) and nucleocapsid (N). In addition, seven putative ORFs encoding accessory proteins are interspersed between the structural genes.

An exemplary nucleic acid sequence for the SARS-CoV-2 ORF1a/b gene is set forth in GenBank accession number MN908947.3 (SEQ ID NO:7):

```
   1 atggagagcc ttgtccctgg tttcaacgag aaaacacacg tccaactcag tttgcctgtt 61 ttacaggttc gcgacgtgct cgtacgtggc tttggagact ccgtggagga ggtcttatca 121 gaggcacgtc aacatcttaa agatggcact tgtggcttag tagaagttga aaaaggcgtt 181 ttgcctcaac ttgaacagcc ctatgtgttc atcaaacgtt cggatgctcg aactgcacct 241 catggtcatg ttatggttga gctggtagca gaactcgaag gcattcagta cggtcgtagt 301 ggtgagacac ttggtgtcct tgtccctcat gtgggcgaaa taccagtggc ttaccgcaag 361 gttcttcttc gtaagaacgg taataaagga gctggtggcc atagttacgg cgccgatcta 421 aagtcatttg acttaggcga cgagcttggc actgatcctt atgaagattt tcaagaaaac 481 tggaacacta aacatagcag tggtgttacc cgtgaactca tgcgtgagct taacggaggg 541 gcatacactc gctatgtcga taacaacttc tgtggccctg atggctaccc tcttgagtgc 601 attaaagacc ttctagcacg tgctggtaaa gcttcatgca ctttgtccga caactggac 661 tttattgaca ctaagagggg tgtatactgc tgccgtgaac atgagcatga aattgcttgg 721 tacacggaac gttctgaaaa gagctatgaa ttgcagacac cttttgaaat taaattggca 781 aagaaatttg acaccttcaa tgggggaatgt ccaaattttg tatttccctt aaattccata 841 atcaagacta ttcaaccaag ggttgaaaag aaaaagcttg atggctttat gggtagaatt 901 cgatctgtct atccagttgc gtcaccaaat gaatgcaacc aaatgtgcct ttcaactctc 961 atgaagtgtg atcattgtgg tgaaacttca tggcagacgg gcgatttttgt aaagccact 1021 tgcgaatttt gtggcactga gaatttgact aaagaaggtg ccactacttg tggttactta 1081 ccccaaaatg ctgttgttaa aatttattgt ccagcatgtc acaattcaga gtaggacct 1141 gagcatagtc ttgccgaata ccataatgaa tctggcttga aaaccattct tcgtaagggt 1201 ggtcgcacta ttgcctttgg aggctgtgtg ttctcttatg ttggttgcca taacaagtgt 1261 gcctattggg ttccacgtgc tagcgctaac ataggttgta accatacagg tgttgttgga 1321 gaaggttccg aaggtcttaa tgacaacctt cttgaaatac tccaaaaga gaaagtcaac 1381 atcaatattg ttggtgactt taaacttaat gaagagatcg ccattatttt ggcatctttt 1441 tctgcttcca caagtgcttt tgtggaaact gtgaaaggtt tggattataa agcattcaaa 1501 caaattgttg aatcctgtgg taattttaaa gttacaaag gaaaagctaa aaaaggtgcc 1561 tggaatattg gtgaacagaa atcaatactg agtcctcttt atgcatttgc atcagaggct 1621 gctcgtgttg tacgatcaat tttctcccgc actcttgaaa ctgctcaaaa ttctgtgcgt 1681 gttttacaga aggccgctat aacaatacta gatggaattt cacagtattc actgagactc 1741 attgatgcta tgatgttcac atctgatttg gctactaaca atctagttgt aatggcctac 1801 attacaggtg gtgttgttca gttgacttcg cagtggctaa ctaacatctt tggcactgtt 1861 tatgaaaaac tcaaaccgt ccttgattgg cttgaagaga gtttaaggaa ggtgtagag 1921 tttcttagag acggttggga aattgttaaa tttatctcaa cctgtgcttg tgaaattgtc
```

-continued

```
1981 ggtggacaaa ttgtcacctg tgcaaaggaa attaaggaga gtgttcagac attctttaag 2041 cttgtaaata aatttttggc tttgtgtgct gactctatca ttattggtgg agctaaactt 2101 aaagccttga atttaggtga aacatttgtc acgcactcaa agggattgta cagaaagtgt 2161 gttaaatcca gagaagaaac tggcctactc atgcctctaa aagccccaaa agaaattatc 2221 ttcttagagg gagaaacact tcccacagaa gtgttaacag aggaagttgt cttgaaaact 2281 ggtgatttac aaccattaga acaacctact agtgaagctg ttgaagctcc attggttggt 2341 acaccagttt gtattaacgg gcttatgttg ctcgaaatca aagacacaga aaagtactgt 2401 gcccttgcac ctaatatgat ggtaacaaac aataccttca cactcaaagg cggtgcacca 2461 acaaaggtta cttttggtga tgacactgtg atagaagtgc aaggttacaa gagtgtgaat 2521 atcacttttg aacttgatga aaggattgat aaagtactta atgagaagtg ctctgcctat 2581 acagttgaac tcggtacaga agtaaatgag ttcgcctgtg ttgtggcaga tgctgtcata 2641 aaaactttgc aaccagtatc tgaattactt acaccactgg gcattgattt agatgagtgg 2701 agtatggcta catactactt atttgatgag tctggtgagt ttaaattggc ttcacatatg 2761 tattgttctt tctaccctcc agatgaggat gaagaagaag gtgattgtga agaagaagag 2821 tttgagccat caactcaata tgagtatggt actgaagatg attaccaagg taaacctttg 2881 gaatttggtg ccacttctgc tgctcttcaa cctgaagaag agcaagaaga agattggtta 2941 gatgatgata gtcaacaaac tgttggtcaa caagacggca gtgaggacaa tcagacaact 3001 actattcaaa caattgttga ggttcaacct caattagaga tggaacttac accagttgtt 3061 cagactattg aagtgaatag ttttagtggt tatttaaaac ttactgacaa tgtatacatt 3121 aaaaatgcag acattgtgga agaagctaaa aaggtaaaac caacagtggt tgttaatgca 3181 gccaatgttt accttaaaca tggaggaggt gttgcaggag ccttaaataa ggctactaac 3241 aatgccatgc aagttgaatc tgatgattac atagctacta atggaccact taaagtgggt 3301 ggtagttgtg tttttaagcgg acacaatctt gctaaacact gtcttcatgt tgtcggccca 3361 aatgttaaca aaggtgaaga cattcaactt cttaagagtg cttatgaaaa tttttaatcag 3421 cacgaagttc tacttgcacc attattatca gctggtattt ttggtgctga ccctatacat 3481 tctttaagag tttgtgtaga tactgttcgc acaaatgtct acttagctgt ctttgataaa 3541 aatctctatg acaaacttgt ttcaagcttt ttggaaatga gagtgaaaa gcaagttgaa 3601 caaaagatcg ctgagattcc taaagaggaa gttaagccat ttataactga aagtaaacct 3661 tcagttgaac agagaaaaca agatgataag aaaatcaaag cttgtgttga agaagttaca 3721 acaactctgg aagaaactaa gttcctcaca gaaaacttgt actttatat tgacattaat 3781 ggcaatcttc atccagattc tgccactctt gttagtgaca ttgacatcac tttcttaaag 3841 aaagatgctc catatatagt gggtgatgtt gttcaagagg gtgtttttaac tgctgtggtt 3901 atacctacta aaaaggctgg tggcactact gaaatgctag cgaaagcttt gagaaaagtg 3961 ccaacagaca attatataac cacttacccg ggtcagggtt aaatggtta cactgtagag 4021 gaggcaaaga cagtgcttaa aaagtgtaaa agtgccttt acattctacc atctattatc 4081 tctaatgaga agcaagaaat tcttggaact gtttcttgga atttgcgaga aatgcttgca 4141 catgcagaag aaacacgcaa attaatgcct gtctgtgtgg aaactaaagc catagtttca 4201 actatacagc gtaaatataa gggtattaaa atacaagagg gtgtggttga ttatggtgct 4261 agatttttact tttcacaccag taaaacaact gtagcgtcac ttatcaacac acttaacgat 4321 ctaaatgaaa ctcttgttac aatgccactt ggctatgtaa cacatggctt aaatttggaa
```

-continued

```
4381 gaagctgctc ggtatatgag atctctcaaa gtgccagcta cagtttctgt ttcttcacct 4441 gatgctgtta cagcgtataa tggttatctt acttcttctt ctaaaacacc tgaagaacat 4501 tttattgaaa ccatctcact tgctggttcc tataaagatt ggtcctattc tggacaatct 4561 acacaactag gtatagaatt tcttaagaga ggtgataaaa gtgtatatta cactagtaat 4621 cctaccacat tccacctaga tggtgaagtt atcacctttg acaatcttaa gacacttctt 4681 tctttgagag aagtgaggac tattaaggtg tttacaacag tagacaacat taacctccac 4741 acgcaagttg tggacatgtc aatgacatat ggacaacagt ttggtccaac ttatttggat 4801 ggagctgatg ttactaaaat aaaacctcat aattcacatg aaggtaaaac attttatgtt 4861 ttacctaatg atgacactct acgtgttgag gcttttgagt actaccacac aactgatcct 4921 agttttctgg gtaggtacat gtcagcatta aatcacacta aaaagtggaa atacccacaa 4981 gttaatggtt taacttctat taaatgggca gataacaact gttatcttgc cactgcattg 5041 ttaacactcc aacaaataga gttgaagttt aatccacctg ctctacaaga tgcttattac 5101 agagcaaggg ctggtgaagc tgctaacttt tgtgcactta tcttagccta ctgtaataag 5161 acagtaggtg agttaggtga tgttagagaa acaatgagtt acttgtttca acatgccaat 5221 ttagattctt gcaaaagagt cttgaacgtg gtgtgtaaaa cttgtggaca acagcagaca 5281 acccttaagg gtgtagaagc tgttatgtac atgggcacac tttcttatga acaatttaag 5341 aaaggtgttc agataccttg tacgtgtggt aaacaagcta caaaatatct agtacaacag 5401 gagtcacctt ttgttatgat gtcagcacca cctgctcagt atgaacttaa gcatggtaca 5461 tttacttgtg ctagtgagta cactggtaat taccagtgtg gtcactataa acatataact 5521 tctaaagaaa ctttgtattg catagacggt gctttactta caaagtcctc agaatacaaa 5581 ggtcctatta cggatgtttt ctacaaagaa aacagttaca caacaaccat aaaaccagtt 5641 acttataaat tggatggtgt tgtttgtaca gaaattgacc ctaagttgga caattattat 5701 aagaaagaca attcttattt cacagagcaa ccaattgatc ttgtaccaaa ccaaccatat 5761 ccaaacgcaa gcttcgataa ttttaagttt gtatgtgata atatcaaatt tgctgatgat 5821 ttaaaccagt taactggtta taagaaacct gcttcaagag agcttaaagt tacattttttc 5881 cctgacttaa atggtgatgt ggtggctatt gattataaac actacacacc ctctttttaag 5941 aaaggagcta aattgttaca taaacctatt gtttggcatg ttaacaatgc aactaataaa 6001 gccacgtata aaccaaatac ctggtgtata cgttgtcttt ggagcacaaa accagttgaa 6061 acatcaaatt cgtttgatgt actgaagtca gaggacgcgc agggaatgga taatcttgcc 6121 tgcgaagatc taaaaccagt ctctgaagaa gtagtggaaa atcctaccat acagaaagac 6181 gttcttgagt gtaatgtgaa aactaccgaa gttgtaggag acattatact taaaccagca 6241 aataatagtt taaaaattac agaagaggtt ggccacacag atctaatggc tgcttatgta 6301 gacaattcta gtcttactat taagaaacct aatgaattat ctagagtatt aggtttgaaa 6361 acccttgcta ctcatggttt agctgctgtt aatagtgtcc cttgggatac tatagctaat 6421 tatgctaagc ctttttcttaa caaagttgtt agtacaacta ctaacatagt tacacggtgt 6481 ttaaaccgtg tttgtactaa ttatatgcct tatttcttta ctttattgct acaattgtgt 6541 actttttacta gaagtacaaa ttctagaatt aaagcatcta tgccgactac tatagcaaag 6601 aatactgtta agagtgtcgg taaattttgt ctagaggctt catttaatta tttgaagtca 6661 cctaattttt ctaaactgat aaatattata atttggtttt tactattaag tgtttgccta 6721 ggttctttaa tctactcaac cgctgcttta ggtgttttaa tgtctaattt aggcatgcct 6781 tcttactgta ctggttacag agaaggctat ttgaactcta ctaatgtcac tattgcaacc
```

-continued

```
6841 tactgtactg gttctatacc ttgtagtgtt tgtcttagtg gtttagattc tttagacacc 6901 tatccttctt tagaaactat acaaattacc atttcatctt ttaaatggga tttaactgct 6961 tttggcttag ttgcagagtg gttttttggca tatattcttt tcactaggtt tttctatgta 7021 cttggattgg ctgcaatcat gcaattgttt ttcagctatt ttgcagtaca ttttattagt 7081 aattcttggc ttatgtggtt aataattaat cttgtacaaa tggccccgat ttcagctatg 7141 gttagaatgt acatcttctt tgcatcattt tattatgtat ggaaaagtta tgtgcatgtt 7201 gtagacggtt gtaattcatc aacttgtatg atgtgttaca aacgtaatag agcaacaaga 7261 gtcgaatgta caactattgt taatggtgtt agaaggtcct tttatgtcta tgctaatgga 7321 ggtaaaggct tttgcaaact acacaattgg aattgtgtta attgtgatac attctgtgct 7381 ggtagtacat ttattagtga tgaagttgcg agagacttgt cactacagtt taaaagacca 7441 ataaatccta ctgaccagtc ttcttacatc gttgatagtg ttacagtgaa gaatggttcc 7501 atccatcttt actttgataa agctggtcaa aagacttatg aaagacattc tctctctcat 7561 tttgttaact tagacaacct gagagctaat aacactaaag gttcattgcc tattaatgtt 7621 atagtttttg atggtaaatc aaaatgtgaa gaatcatctg caaaatcagc gtctgtttac 7681 tacagtcagc ttatgtgtca acctatactg ttactagatc aggcattagt gtctgatgtt 7741 ggtgatagtg cggaagttgc agttaaaatg tttgatgctt acgttaatac gttttcatca 7801 acttttaacg taccaatgga aaaactcaaa acactagttg caactgcaga agctgaactt 7861 gcaaagaatg tgtccttaga caatgtctta tctactttta tttcagcagc tcggcaaggg 7921 tttgttgatt cagatgtaga aactaaagat gttgttgaat gtcttaaatt gtcacatcaa 7981 tctgacatag aagttactgg cgatagttgt aataactata tgctcaccta taacaaagtt 8041 gaaaacatga cacccgtga ccttggtgct tgtattgact gtagtgcgcg tcatattaat 8101 gcgcaggtag caaaaagtca caacattgct ttgatatgga cgttaaaga tttcatgtca 8161 ttgtctgaac aactacgaaa acaaatacgt agtgctgcta aaaagaataa cttacctttt 8221 aagttgacat gtgcaactac tagacaagtt gttaatgttg taacaacaaa gatagcactt 8281 aagggtggta aaattgttaa taattggttg aagcagttaa ttaaagttac acttgtgttc 8341 cttttttgttg ctgctatttt ctatttaata acacctgttc atgtcatgtc taaacatact 8401 gactttttcaa gtgaaatcat aggatacaag gctattgatg gtggtgtcac tcgtgacata 8461 gcatctacag atacttgttt tgctaacaaa catgctgatt ttgacacatg gtttagccag 8521 cgtggtggta gttatactaa tgacaaagct tgcccattga ttgctgcagt cataacaaga 8581 gaagtgggtt ttgtcgtgcc tggtttgcct ggcacgatat tacgcacaac taatggtgac 8641 tttttgcatt tcttacctag agttttttagt gcagttggta acatctgtta cacaccatca 8701 aaacttatag agtacactga ctttgcaaca tcagcttgtg ttttggctgc tgaatgtaca 8761 attttttaaag atgcttctgg taagccagta ccatattgtt atgataccaa tgtactagaa 8821 ggttctgttg cttatgaaag tttacgccct gacacacgtt atgtgctcat ggatggctct 8881 attattcaat ttcctaacac ctaccttgaa ggttctgtta gagtggtaac aacttttgat 8941 tctgagtact gtaggcacgg cacttgtgaa agatcagaag ctggtgtttg tgtatctact 9001 agtggtagat gggtacttaa caatgattat tacagatctt taccaggagt tttctgtggt 9061 gtagatgctg taaatttact tactaatatg tttacaccac taattcaacc tattggtgct 9121 ttggacatat cagcatctat agtagctggt ggtattgtag ctatcgtagt aacatgcctt 9181 gcctactatt ttatgaggtt tagaagagct tttggtgaat acagtcatgt agttgccttt
```

-continued

```
 9241 aatactttac tattccttat gtcattcact gtactctgtt taacaccagt ttactcattc 9301 ttacctggtg tttattctgt tatttacttg tacttgacat tttatcttac taatgatgtt 9361 tctttttttag cacatattca gtggatggtt atgttcacac ctttagtacc tttctggata 9421 acaattgctt atatcatttg tatttccaca aagcatttct attggttctt tagtaattac 9481 ctaaagagac gtgtagtctt taatggtgtt tcctttagta cttttgaaga agctgcgctg 9541 tgcacctttt tgttaaataa agaaatgtat ctaaagttgc gtagtgatgt gctattacct 9601 cttacgcaat ataatagata cttagctctt tataataagt acaagtattt tagtggagca 9661 atggatacaa ctagctacag agaagctgct tgttgtcatc tcgcaaaggc tctcaatgac 9721 ttcagtaact caggttctga tgttctttac caaccaccac aaacctctat cacctcagct 9781 gttttgcaga gtggttttag aaaaatggca ttcccatctg gtaaagttga gggttgtatg 9841 gtacaagtaa cttgtggtac aactacactt aacggtctttt ggcttgatga cgtagtttac 9901 tgtccaagac atgtgatctg cacctctgaa gacatgctta accctaatta tgaagattta 9961 ctcattcgta agtctaatca taatttcttg gtacaggctg gtaatgttca actcagggtt 10021 attggacatt ctatgcaaaa ttgtgtactt aagcttaagg ttgatacagc caatcctaag 10081 acacctaagt ataagtttgt tcgcattcaa ccaggacaga ctttttcagt gttagcttgt 10141 tacaatggtt caccatctgg tgtttaccaa tgtgctatga ggcccaattt cactattaag 10201 ggttcattcc ttaatggttc atgtggtagt gttggttta acatagatta tgactgtgtc 10261 tcttttttgtt acatgcacca tatggaatta ccaactggag ttcatgctgg cacagactta 10321 gaaggtaact tttatggacc ttttgttgac aggcaaacag cacaagcagc tggtacggac 10381 acaactatta cagttaatgt tttagcttgg ttgtacgctg ctgttataaa tggagacagg 10441 tggtttctca atcgatttac cacaactctt aatgacttta accttgtggc tatgaagtac 10501 aattatgaac ctctaacaca agaccatgtt gacatactag gacctctttc tgctcaaact 10561 ggaattgccg tttttagatat gtgtgcttca ttaaaagaat tactgcaaaa tggtatgaat 10621 ggacgtacca tattgggtag tgctttatta gaagatgaat ttacaccttt tgatgttgtt 10681 agacaatgct caggtgttac tttccaaagt gcagtgaaaa gaacaatcaa gggtacacac 10741 cactggttgt tactcacaat tttgacttca cttttagttt tagtccagag tactcaatgg 10801 tctttgttct tttttttgta tgaaaatgcc tttttacctt ttgctatggg tattattgct 10861 atgtctgctt ttgcaatgat gtttgtcaaa cataagcatg catttctctg tttgttttttg 10921 ttaccttctc ttgccactgt agcttatttt aatatggtct atatgcctgc tagttgggtg 10981 atgcgtatta tgacatggtt ggatatggtt gatactagtt tgtctggttt taagctaaaa 11041 gactgtgtta tgtatgcatc agctgtagtg ttactaatcc ttatgacagc aagaactgtg 11101 tatgatgatg gtgctaggag agtgtggaca cttatgaatg tcttgacact cgtttataaa 11161 gtttattatg gtaatgcttt agatcaagcc atttccatgt gggctcttat aatctctgtt 11221 acttctaact actcaggtgt agttacaact gtcatgtttt tggccagagg tattgttttt 11281 atgtgtgttg agtattgccc tattttcttc ataactggta atacacttca gtgtataatg 11341 ctagtttatt gtttcttagg ctatttttgt acttgttact ttggcctctt ttgtttactc 11401 aaccgctact ttagactgac tcttggtgtt tatgattact agtttctac acaggagttt 11461 agatatatga attcacaggg actactccca cccaagaata gcatagatgc cttcaaactc 11521 aacattaaat tgttgggtgt tggtggcaaa ccttgtatca agtagccac tgtacagtct 11581 aaaatgtcag atgtaaagtg cacatcagta gtcttactct cagtttttgca acaactcaga 11641 gtagaatcat catctaaatt gtgggctcaa tgtgtccagt tacacaatga cattctctta
```

-continued

```
11701 gctaaagata ctactgaagc ctttgaaaaa atggtttcac tactttctgt tttgctttcc 11761 atgcagggtg ctgtagacat aaacaagctt tgtgaagaaa tgctggacaa cagggcaacc 11821 ttacaagcta tagcctcaga gtttagttcc cttccatcat atgcagcttt tgctactgct 11881 caagaagctt atgagcaggc tgttgctaat ggtgattctg aagttgttct taaaaagttg 11941 aagaagtctt tgaatgtggc taaatctgaa tttgaccgtg atgcagccat gcaacgtaag 12001 ttggaaaaga tggctgatca agctatgacc caaatgtata aacaggctag atctgaggac 12061 aagagggcaa aagttactag tgctatgcag acaatgcttt tcactatgct tagaaagttg 12121 gataatgatg cactcaacaa cattatcaac aatgcaagag atggttgtgt tcccttgaac 12181 ataatacctc ttacaacagc agccaaacta atggttgtca taccagacta taacacatat 12241 aaaaatacgt gtgatggtac aacatttact tatgcatcag cattgtggga aatccaacag 12301 gttgtagatg cagatagtaa aattgttcaa cttagtgaaa ttagtatgga caattcacct 12361 aatttagcat ggcctcttat tgtaacagct ttaagggcca attctgctgt caaattacag 12421 aataatgagc ttagtcctgt tgcactacga cagatgtctt gtgctgccgg tactacacaa 12481 actgcttgca ctgatgacaa tgcgttagct tactacaaca caacaaaggg aggtaggttt 12541 gtacttgcac tgttatccga tttacaggat ttgaaatggg ctagattccc taagagtgat 12601 ggaactggta ctatctatac agaactggaa ccaccttgta ggtttgttac agacacacct 12661 aaaggtccta aagtgaagta tttatacttt attaaaggat taaacaacct aaatagaggt 12721 atggtacttg gtagtttagc tgccacagta cgtctacaag ctggtaatgc aacagaagtg 12781 cctgccaatt caactgtatt atctttctgt gcttttgctg tagatgctgc taaagcttac 12841 aaagattatc tagctagtgg gggacaacca atcactaatt gtgttaagat gttgtgtaca 12901 cacactggta ctggtcaggc aataacagtt acaccggaag ccaatatgga tcaagaatcc 12961 tttggtggtg catcgtgttg tctgtactgc cgttgccaca tagatcatcc aaatcctaaa 13021 ggattttgtg acttaaaagg taagtatgta caaataccta caacttgtgc taatgaccct 13081 gtgggtttta cacttaaaaa cacagtctgt accgtctgcg gtatgtggaa aggttatggc 13141 tgtagttgtg atcaactccg cgaacccatg cttcagtcag ctgatgcaca atcgttttta 13201 aaccgggttt gcggtgtaag tgcagcccgt cttacaccgt gcggcacagg cactagtact 13261 gatgtcgtat acagggcttt tgacatctac aatgataaag tagctggttt tgctaaattc 13321 ctaaaaacta attgttgtcg cttccaagaa aaggacgaag atgacaattt aattgattct 13381 tactttgtag ttaagagaca cactttctct aactaccaac atgaagaaac aatttataat 13441 ttacttaagg attgtccagc tgttgctaaa catgacttct ttaagtttag aatagacggt 13501 gacatggtac cacatatatc acgtcaacgt cttactaaat acacaatggc agacctcgtc 13561 tatgctttaa ggcattttga tgaaggtaat tgtgacacat aaaagaaat acttgtcaca 13621 tacaattgtt gtgatgatga ttatttcaat aaaaaggact ggtatgattt tgtagaaaac 13681 ccagatatat tacgcgtata cgccaactta ggtgaacgtg tacgccaagc tttgttaaaa 13741 acagtacaat tctgtgatgc catgcgaaat gctggtattg ttggtgtact gacattagat 13801 aatcaagatc tcaatggtaa ctggtatgat ttcggtgatt tcatacaaac cacgccaggt 13861 agtggagttc ctgttgtaga ttcttattat tcattgttaa tgcctatatt aaccttgacc 13921 agggctttaa ctgcagagtc acatgttgac actgacttaa caaagcctta cattaagtgg 13981 gatttgttaa aatatgactt cacggaagag aggttaaaac tctttgaccg ttattttaaa 14041 tattgggatc agacatacca cccaaattgt gttaactgtt tggatgacag atgcattctg
```

-continued

```
14101 cattgtgcaa actttaatgt tttattctct acagtgttcc cacctacaag ttttggacca 14161 ctagtgagaa aaatatttgt tgatggtgtt ccatttgtag tttcaactga ataccacttc 14221 agagagctag gtgttgtaca taatcaggat gtaaacttac atagctctag acttagtttt 14281 aaggaattac ttgtgtatgc tgctgaccct gctatgcacg ctgcttctgg taatctatta 14341 ctagataaac gcactacgtg cttttcagta gctgcactta ctaacaatgt tgcttttcaa 14401 actgtcaaac ccggtaattt taacaaagac ttctatgact ttgctgtgtc taagggtttc 14461 tttaaggaag gaagttctgt tgaattaaaa cacttcttct ttgctcagga tggtaatgct 14521 gctatcagcg attatgacta ctatcgttat aatctaccaa caatgtgtga tatcagacaa 14581 ctactatttg tagttgaagt tgttgataag tactttgatt gttacgatgg tggctgtatt 14641 aatgctaacc aagtcatcgt caacaaccta gacaaatcag ctggttttcc atttaataaa 14701 tggggtaagg ctagacttta ttatgattca atgagttatg aggatcaaga tgcacttttc 14761 gcatatacaa aacgtaatgt catccctact ataactcaaa tgaatcttaa gtatgccatt 14821 agtgcaaaga atagagctcg caccgtagct ggtgtctcta tctgtagtac tatgaccaat 14881 agacagtttc atcaaaaatt attgaaatca atagccgcca ctagaggagc tactgtagta 14941 attggaacaa gcaaattcta tggtggttgg cacaacatgt aaaaaactgt ttatagtgat 15001 gtagaaaacc ctcaccttat gggttgggat tatcctaaat gtgatagagc catgcctaac 15061 atgcttagaa ttatggcctc acttgttctt gctcgcaaac atacaacgtg ttgtagcttg 15121 tcacaccgtt tctatagatt agctaatgag tgtgctcaag tattgagtga aatggtcatg 15181 tgtggcggtt cactatatgt taaaccaggt ggaacctcat caggagatgc cacaactgct 15241 tatgctaata gtgttttttaa catttgtcaa gctgtcacgg ccaatgttaa tgcactttta 15301 tctactgatg gtaacaaaat tgccgataag tatgtccgca atttacaaca cagactttat 15361 gagtgtctct atagaaatag agatgttgac acagactttg tgaatgagtt ttacgcatat 15421 ttgcgtaaac atttctcaat gatgatactc tctgacgatg ctgttgtgtg tttcaatagc 15481 acttatgcat ctcaaggtct agtggctagc ataaagaact ttaagtcagt tctttattat 15541 caaaacaatg tttttatgtc tgaagcaaaa tgttggactg agactgacct tactaaagga 15601 cctcatgaat tttgctctca acatacaatg ctagttaaac agggtgatga ttatgtgtac 15661 cttccttacc cagatccatc aagaatccta ggggccggct gttttgtaga tgatatcgta 15721 aaaacagatg gtacacttat gattgaacgg ttcgtgtctt agctataga tgcttaccca 15781 cttactaaac atcctaatca ggagtatgct gatgtctttc atttgtactt acaatacata 15841 agaaagctac atgatgagtt aacaggacac atgttagaca tgtattctgt tatgcttact 15901 aatgataaca cttcaaggta ttgggaacct gagtttttatg aggctatgta cacaccgcat 15961 acagtcttac aggctgttgg ggcttgtgtt ctttgcaatt cacagacttc attaagatgt 16021 ggtgcttgca tacgtagacc attcttatgt tgtaaatgct gttacgacca tgtcatatca 16081 acatcacata aattagtctt gtctgttaat ccgtatgttt gcaatgctcc aggttgtgat 16141 gtcacagatg tgactcaact ttacttagga ggtatgagct attattgtaa atcacataaa 16201 ccacccatta gttttccatt gtgtgctaat ggacaagttt ttggtttata taaaaataca 16261 tgtgttggta gcgataatgt tactgacttt aatgcaattg caacatgtga ctggacaaat 16321 gctggtgatt acatttttagc taacacctgt actgaaagac tcaagctttt tgcagcagaa 16381 acgctcaaag ctactgagga gacatttaaa ctgtcttatg gtattgctac tgtacgtgaa 16441 gtgctgtctg acagagaatt acatctttca tgggaagttg gtaaacctag accaccactt 16501 aaccgaaatt atgtctttac tggttatcgt gtaactaaaa acagtaaagt acaaatagga
```

-continued

```
16561 gagtacacct ttgaaaaagg tgactatggt gatgctgttg tttaccgagg tacaacaact 16621 tacaaattaa atgttggtga ttattttgtg ctgacatcac atacagtaat gccattaagt 16681 gcacctacac tagtgccaca agagcactat gttagaatta ctggcttata cccaacactc 16741 aatatctcag atgagttttc tagcaatgtt gcaaattatc aaaaggttgg tatgcaaaag 16801 tattctacac tccagggacc acctggtact ggtaagagtc attttgctat tggcctagct 16861 ctctactacc cttctgctcg catagtgtat acagcttgct ctcatgccgc tgttgatgca 16921 ctatgtgaga aggcattaaa atatttgcct atagataaat gtagtagaat tatacctgca 16981 cgtgctcgtg tagagtgttt tgataaattc aaagtgaatt caacattaga acagtatgtc 17041 ttttgtactg taaatgcatt gcctgagacg acagcagata tagttgtctt tgatgaaatt 17101 tcaatggcca caaattatga tttgagtgtt gtcaatgcca gattacgtgc taagcactat 17161 gtgtacattg gcgaccctgc tcaattacct gcaccacgca cattgctaac taagggcaca 17221 ctagaaccag aatatttcaa ttcagtgtgt agacttatga aaactatagg tccagacatg 17281 ttcctcggaa cttgtcggcg ttgtcctgct gaaattgttg acactgtgag tgctttggtt 17341 tatgataata agcttaaagc acataaagac aaatcagctc aatgctttaa aatgttttat 17401 aagggtgtta tcacgcatga tgtttcatct gcaattaaca ggccacaaat aggcgtggta 17461 agagaattcc ttacacgtaa ccctgcttgg agaaaagctg tctttatttc accttataat 17521 tcacagaatg ctgtagcctc aaagattttg ggactaccaa ctcaaactgt tgattcatca 17581 cagggctcag aatatgacta tgtcatattc actcaaacca ctgaaacagc tcactcttgt 17641 aatgtaaaca gatttaatgt tgctattacc agagcaaaag taggcatact ttgcataatg 17701 tctgatagag acctttatga caagttgcaa tttacaagtc ttgaaattcc acgtaggaat 17761 gtggcaactt tacaagctga aaatgtaaca ggactcttta agattgtag taaggtaatc 17821 actgggttac atcctacaca ggcacctaca cacctcagtg ttgacactaa attcaaaact 17881 gaaggtttat gtgttgacat acctggcata cctaaggaca tgacctatag aagactcatc 17941 tctatgatgg gttttaaaat gaattatcaa gttaatggtt accctaacat gtttatcacc 18001 cgcgaagaag ctataagaca tgtacgtgca tggattggct tcgatgtcga ggggtgtcat 18061 gctactagag aagctgttgg taccaattta cctttacagc taggtttttc tacaggtgtt 18121 aacctagttg ctgtacctac aggttatgtt gatacaccta ataatacaga tttttccaga 18181 gttagtgcta aaccaccgcc tggagatcaa tttaaacacc tcataccact tatgtacaaa 18241 ggacttcctt ggaatgtagt gcgtataaag attgtacaaa tgttaagtga cacacttaaa 18301 aatctctctg acagagtcgt atttgtctta tgggcacatg gctttgagtt gacatctatg 18361 aagtattttg tgaaaatagg acctgagcgc acctgttgtc tatgtgatag acgtgccaca 18421 tgcttttcca ctgcttcaga cacttatgcc tgttggcatc attctattgg atttgattac 18481 gtctataatc cgtttatgat tgatgttcaa caatgggtt ttacaggtaa cctacaaagc 18541 aaccatgatc tgtattgtca gtccatggt aatgcacatg tagctagttg tgatgcaatc 18601 atgactaggt gtctagctgt ccacgagtgc tttgttaagc gtgttgactg gactattgaa 18661 tatcctataa ttggtgatga actgaagatt aatgcggctt gtagaaaggt tcaacacatg 18721 gttgttaaag ctgcattatt agcagacaaa ttcccagttc ttcacgacat tggtaaccct 18781 aaagctatta gtgtgtacc tcaagctgat gtagaatgga gttctatga tgcacagcct 18841 tgtagtgaca aagcttataa aatagaagaa ttattctatt cttatgccac acattctgac 18901 aaattcacag atggtgtatg cctattttgg aattgcaatg tcgatagata tcctgctaat
```

-continued

```
18961 tccattgttt gtagatttga cactagagtg ctatctaacc ttaacttgcc tggttgtgat 19021 ggtggcagtt tgtatgtaaa taaacatgca ttccacacac cagcttttga taaaagtgct 19081 tttgttaatt taaaacaatt accatttttc tattactctg acagtccatg tgagtctcat 19141 ggaaaacaag tagtgtcaga tatagattat gtaccactaa agtctgctac gtgtataaca 19201 cgttgcaatt taggtggtgc tgtctgtaga catcatgcta atgagtacag attgtatctc 19261 gatgcttata acatgatgat ctcagctggc tttagcttgt gggtttacaa acaatttgat 19321 acttataacc tctggaacac ttttacaaga cttcagagtt tagaaaatgt ggcttttaat 19381 gttgtaaata agggacactt tgatggacaa cagggtgaag taccagtttc tatcattaat 19441 aacactgttt acacaaaagt tgatggtgtt gatgtagaat tgtttgaaaa taaaacaaca 19501 ttacctgtta atgtagcatt tgagctttgg gctaagcgca acattaaacc agtaccagag 19561 gtgaaaatac tcaataattt gggtgtggac attgctgcta atactgtgat ctgggactac 19621 aaaagagatg ctccagcaca tatatctact attggtgttt gttctatgac tgacatagcc 19681 aagaaaccaa ctgaaacgat ttgtgcacca ctcactgtct tttttgatgg tagagttgat 19741 ggtcaagtag acttatttag aaatgcccgt aatggtgttc ttattacaga aggtagtgtt 19801 aaaggtttac aaccatctgt aggtcccaaa caagctagtc ttaatggagt cacattaatt 19861 ggagaagccg taaaaacaca gttcaattat tataagaaag ttgatggtgt tgtccaacaa 19921 ttacctgaaa cttactttac tcagagtaga aatttacaag aatttaaacc caggagtcaa 19981 atggaaattg atttcttaga attagctatg gatgaattca ttgaacggta taaattagaa 20041 ggctatgcct tcgaacatat cgtttatgga gattttagtc atagtcagtt aggtggttta 20101 catctactga ttggactagc taaacgtttt aaggaatcac cttttgaatt agaagatttt 20161 attcctatgg acagtacagt taaaaactat ttcataacag atgcgcaaac aggttcatct 20221 aagtgtgtgt gttctgttat tgatttatta cttgatgatt ttgttgaaat aataaaatcc 20281 caagatttat ctgtagtttc taaggttgtc aaagtgacta ttgactatac agaaatttca 20341 tttatgcttt ggtgtaaaga tggccatgta gaaacatttt acccaaaatt acaatctagt 20401 caagcgtggc aaccgggtgt tgctatgcct aatctttaca aaatgcaaag aatgctatta 20461 gaaaagtgtg accttcaaaa ttatggtgat agtgcaacat tacctaaagg cataatgatg 20521 aatgtcgcaa aatatactca actgtgtcaa tatttaaaca cattaacatt agctgtaccc 20581 tataatatga gagttataca ttttggtgct ggttctgata aaggagttgc accaggtaca 20641 gctgttttaa gacagtggtt gcctacgggt acgctgcttg tcgattcaga tcttaatgac 20701 tttgtctctg atgcagattc aactttgatt ggtgattgtg caactgtaca tacagctaat 20761 aaatgggatc tcattattag tgatatgtac gaccctaaga ctaaaaatgt tacaaaagaa 20821 aatgactcta agagggtttt tttcacttac atttgtgggt ttatacaaca aaagctagct 20881 cttggaggtt ccgtggctat aaagataaca gaacattctt ggaatgctga tctttataag 20941 ctcatgggac acttcgcatg gtggacagcc tttgttacta atgtgaatgc gtcatcatct 21001 gaagcatttt taattggatg taattatctt ggcaaaccac gcgaacaaat agatggttat 21061 gtcatgcatg caaattacat attttggagg aatacaaatc caattcagtt gtcttcctat 21121 tctttatttg acatgagtaa atttcccctt aaattaaggg gtactgctgt tatgtcttta 21181 aaagaaggtc aaatcaatga tatgatttta tctcttctta gtaaaggtag acttataatt 21241 agagaaaaca acagagttgt tatttctagt gatgttcttg ttaacaacta a
```

An exemplary nucleic acid sequence for the SARS-CoV-2 N gene is set forth in GenBank accession number MN908947.3 (SEQ ID NO:8):

```
   1 atgtctgata atggacccca aaatcagcga aatgcacccc gcattacgtt tggtggaccc 61 tcagattcaa ctggcagtaa ccagaatgga gaacgcagtg gggcgcgatc aaaacaacgt 121 cggccccaag gtttacccaa taatactgcg tcttggttca ccgctctcac tcaacatggc 181 aaggaagacc ttaaattccc tcgaggacaa ggcgttccaa ttaacaccaa tagcagtcca 241 gatgaccaaa ttggctacta ccgaagagct accagacgaa ttcgtggtgg tgacggtaaa 301 atgaaagatc tcagtccaag atggtatttc tactacctag gaactgggcc agaagctgga 361 cttccctatg gtgctaacaa agacggcatc atatgggttg caactgaggg agccttgaat 421 acaccaaaag atcacattgg cacccgcaat cctgctaaca atgctgcaat cgtgctacaa 481 cttcctcaag gaacaacatt gccaaaaggc ttctacgcag aagggagcag aggcggcagt 541 caagcctctt ctcgttcctc atcacgtagt cgcaacagtt caagaaattc aactccaggc 601 agcagtaggg gaacttctcc tgctagaatg gctggcaatg gcggtgatgc tgctcttgct 661 ttgctgctgc ttgacagatt gaaccagctt gagagcaaaa tgtctggtaa aggccaacaa 721 caacaaggcc aaactgtcac taagaaatct gctgctgagg cttctaagaa gcctcggcaa 781 aaacgtactg ccactaaagc atacaatgta acacaagctt tcggcagacg tggtccagaa 841 caaacccaag gaaattttgg ggaccaggaa ctaatcagac aaggaactga ttacaaacat 901 tggccgcaaa ttgcacaatt tgcccccagc gcttcagcgt tcttcggaat gtcgcgcatt 961 ggcatggaag tcacaccttc gggaacgtgg ttgacctaca caggtgccat caaattggat 1021 gacaaagatc caaatttcaa agatcaagtc attttgctga ataagcatat tgacgcatac 1081 aaacattcc accaacaga gcctaaaaag gacaaaaaga agaaggctga tgaaactcaa
```

-continued
```
1141 gccttaccgc agagacagaa gaaacagcaa actgtgactc ttcttcctgc tgcagatttg 1201 gatgatttct ccaaacaatt gcaacaatcc atgagcagtg ctgactcaac tcaggcctaa
```

B. Samples

The described systems and compositions detect and/or quantify SARS-CoV-2 virus RNA present within a test or "input" sample that is a liquid. In some forms, an input sample is diluted, concentrated, or otherwise obtained from a liquid, gel, emulsion, or a solid, such as a powder. The described systems and compositions produce an "output" sample, including the products of the RT-qPCR, which include an amplified product labelled with the probe, based on the presence of the SARS-CoV-2 virus present within a test or "input" sample 1. Input Samples for RT-qPCR The described systems include an input sample containing purified RNA and/or DNA. In some forms, the input sample is the product of a process to extract and isolate viral RNA from a biological or environmental sample, such as a biological fluid obtained from a human patient. Therefore, in some forms, an input sample includes an isolated and/or purified RNA, or virus, or mixture of viruses isolated from a biological sample. Extracted and/or purified viral RNA for use as an input sample according to the described systems can be obtained from a biological sample by methods known in the art for purification of RNA. Exemplary purification processes are implemented within the QIAamp Viral RNA Mini Kit, commercially available from Qiagen, and the QIAprep Spin Miniprep Kit for DNA plasmid purification, commercially available from Qiagen Typically, RNA for use as an input sample is extracted from about 0.1 µL to about 1 L of sample, preferably about 140 µL of sample, and eluted in 60 µL elution buffer containing poly(A) carrier RNA.

In some forms, the input sample includes an isolated and/or purified viral nucleic acid, such as an RNA or DNA. RNA or DNA may be present within the sample in the form of intact viral genomic RNA, or fragments of viral genomic RNA. In some forms, the sample includes an isolated and/or purified nucleic acid, such as an RNA or DNA plasmid. In some forms, the input sample is in the form of a cell-free, clarified, aqueous solution. In other forms, the sample includes one or more isolated and/or purified tissues or cells. The one or more tissues or cells can include the SARS-CoV-2 virus within, or bound to or otherwise associated with the one or more cells. Typically, input samples for use in the described assays are in a volume between about 0.1 µL to about 1000 µL, inclusive, preferably in a volume of about 3-5 µL, most preferably a volume of about 4 µL.

2. Origin of Input Samples

Input samples for use in the described assays can originate from any source, including liquids, frozen liquids, or powders, such as freeze-dried or lyophilized samples. In some forms, the input sample is obtained from a biological source, such as one or more tissues, cells, or bodily fluids of a subject. In other forms, the input sample is obtained from an environmental source, such as a sample of water, ice, soil, or a sample obtained from a non-biological source, such as the surface of an object. In some forms the input sample is obtained from a biological fluid of undetermined origin from a subject. In some forms, the origin of the sample is a human patient, such as a patient identified or suspected of having a disease, such as a respiratory or circulatory disease or disorder. Therefore, in preferred forms, an input sample for use in the described assays for detection and/or quantitation of SARS-CoV-2 virus is obtained by isolation of RNA from a biological sample of bodily fluids taken from a human subject. Exemplary bodily fluids include sputum, saliva, mucus, blood, serum, tears, sweat, urine, semen, fluids from the respiratory tract, gastric fluid, fluids from the digestive tract, fluids from the urogenital tract, spinal fluid, ocular fluid, synovial fluid, feces, pus, bile, or other biological fluid. In some forms a sample contains a mixture of two or more biological fluids. In some forms, a biological sample from a patient contains biological fluids of undetermined origin from a subject. In some forms, a sample contains biological fluids of undetermined origin from a subject.

In some forms, the biological sample is contained within in a container, or together with one or more devices used to obtain the sample, such as a swab, syringe, and cotton bud, inoculating loop or other apparatus for obtaining a biological sample from a subject. Therefore, in some forms, the sample includes one or more components associated with the collection device.

3. Controls Samples

In some forms, the assay includes one or more control samples which act as a control for the specificy, detection and quantification of the SARS-CoV-2 virus within. Exemplary negative control samples include purified RNA or DNA derived from viruses that share little or no genetic relatedness with the SARS-CoV-2 virus. Exemplary negative control viruses include RNA extracted from human coronaviruses 229E, OC43, HKU1, NL63, and OC43, MERS, camel coronavirus HKU23, human influenza A viruses (H1N1, H3N2, H5N1, and H7N9 subtypes), avian influenza (H1, H4, H6, and H9 subtypes), human influenza B viruses (Yamagata and Victoria lineages), and adenovirus, enterovirus, human parainfluenza viruses (PIV1, 2, 3 and 4), respiratory syncytial virus, human metapneumovirus, rhinovirus and human bocavirus. In some forms, negative controls can include RNA extracted from retrospective human respiratory specimens previously tested positive for any of these viruses. In some forms, the negative controls are recombinantly-produced nucleic acid vectors which lack one or more of the nucleic acid sequences required for the activity of the designed primer and probe sets that are to be used. In other forms, RNA extracted from sputum samples from patients without respiratory viral infections are negative controls.

In some forms, positive controls to confirm the specificity and efficacy of the assay for detecting and quantifying the SARS-CoV-2 virus include viral RNA extracted from SARS-CoV-2-infected cells, as well as the RTPCR products of SARS coronavirus generated by the ORF1b and N gene assays, cloned into plasmids.

In some forms, RNA or DNA control samples are serially diluted, to evaluate the performance of the assays.

4. Diluents, Fillers and Preservatives

In some forms, the input sample includes a diluent, filler, excipient, or preservative. In some forms, the sample includes one or more reagents which function to preserve or maintain the SARS-CoV-2 virus within the sample. In some forms, the input sample includes one or more reagents that prevent or reduce the activity of RNAse enzymes.

C. Designed Nucleic Acid Oligonucleotide Primers and Probes

The described systems include matched sets of 5' ("forward") and 3' ("reverse") nucleic acid oligonucleotide primers configured to selectively amplify specific fragments of the SARS-CoV-2 virus genome ("amplicons"), as well as target-specific nucleic acid oligonucleotide probes configured to selectively detect/label the resulting amplicons.

Each matched set of primers includes a 5' ("forward") and 3' ("reverse") primer, designed to target and amplify a pre-determined fragment of one or more components of the SARS-CoV-2 virus genome. In some forms, a matched set of primers is designed to amplify a specific fragment of a single target gene of the SARS-CoV-2 virus. Exemplary genes that can be targeted include the viral replicase (ORF1a/ORF1b) gene, the viral spike (S) gene, the viral envelope (E) gene, the viral membrane (M) gene, and the viral nucleocapsid (N) gene. In other forms, a set of matched primers is designed to amplify a specific fragment of a region of the viral genome coding for a non-structural gene, or a fragment of the viral genome spanning two viral genes. Typically, a matched set of primers is designed based on the nucleic acid sequence of the genome of a currently circulating viral strain, for example, Genbank Accession number: MN908947. Exemplary target genes include the nucleic acid sequences of the ORF1a/b gene (SEQ ID NO:7) and N gene (SEQ ID NO:8) of the SARS-CoV-2 virus (Genbank Accession number: MN908947).

RNA viral genomes are more prone to genetic variation due to mutation than DNA viral genomes. Therefore, in some forms, primer sets are designed to recognize and amplify a sequence region that is highly conserved amongst sarbecoviruses, such that mutation of the viral RNA genome over time is less likely to impact the efficacy of the primers for viral detection. In some forms, primer sets are designed based on phylogenetic analyses of multiple viral genomes, to identify conserved primer sites that will bind and amplify the corresponding fragment of multiple related viral genomes. Therefore, in some forms, the design and selection of primer sets provides a means for selecting the extent of genetic diversity among circulating sarbecoviruses for which the assay will be effective. For example, primers can be designed to be specific for one or more specific strains of the SARS-CoV-2 virus. In an exemplary form, the alignment of viral gene sequences from multiple variants of SARS-CoV-2 viruses is carried out using the neighbor joining method, for example, as implemented within the computer program Molecular Evolutionary Genetics Analysis version 10 (MEGA X).

In some forms, primers for detection of SARS-CoV-2 viruses include primers designed to amplify a region of the SARS-CoV-2 virus ORF1b gene that is conserved across the SARS-CoV-2 and SARS-CoV (Urbani strain) virus identified in 2003 (See FIG. 1A).

In a preferred form, the RT-qPCR forward primer sequence for the SARS-CoV-2 virus ORF1b gene is: 5'-TGGGGYTTTACRGGTAACCT-3' (Y=C/T, R=A/G) (SEQ ID NO:1).

In a preferred form, the RT-qPCR reverse primer sequence for the SARS-CoV-2 virus ORF1b gene is: 5'-AACRCGCTTAACAAAGCACTC-3' (R=A/G) (SEQ ID NO:2). When using these primers, the expected amplicon size of the amplified ORF1b gene fragment is 132 bp.

In a preferred form, the sequence of the probe for detecting the presence of the amplified gene fragment is: 5'-TAGTTGTGATGCWATCATGACTAG-3'      (5'-FAM/ZEN/3'-IBFQ format; W=A/T) (SEQ ID NO:3).

Figure 1B:
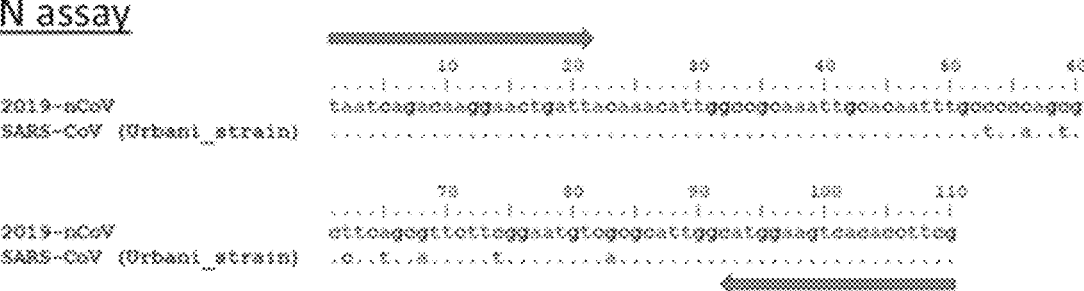

In some forms, primers for detection of SARS-CoV-2 viruses include primers designed to amplify a region of the SARS-CoV-2 virus N gene that is conserved across the SARS-CoV-2 and SARS-CoV (Urbani strain) virus identified in 2003 (See FIG. 1B).

In a preferred form, the RT-qPCR forward primer sequence for the SARS-CoV-2 virus N gene is: 5'-TAATCA-GACAAGGAACTGATTA-3' (SEQ ID NO:4). In a preferred form, the RT-qPCR reverse primer sequence for the SARS-CoV-2 virus N gene is: 5'-CGAAGGTGTGACTTC-CATG-3' (SEQ ID NO:5). When using these primers, the expected size of the amplified N gene fragment is 110 base pairs. In a preferred form, the probe for detecting the presence of the amplified gene fragment is: 5'-GCAAAT-TGTGCAATTTGCGG-3' (5'-FAM/ZEN/3'-IBFQ format) (SEQ ID NO:6).

Variants and modifications of the described nucleic acid oligonucleotide primers and probes which are functional for the specific amplification and labelling of viral RNA and amplicons, respectively, are also described. For example, nucleic acid oligonucleotide primers with a sequence having at least 90%, 95%, 96%, 97%, 98%, or 99% sequence identity to any one of SEQ ID NOS:1, 2, 4 or 5, and which also selectively bind to the corresponding regions of the SARS-CoV-2 virus are also described. Nucleic acid oligonucleotide probes with a sequence having at least 90%, 95%, 96%, 97%, 98%, or 99% sequence identity to any one of SEQ ID NOs:3 or 6, and which also selectively bind to the corresponding fragments of the SARS-CoV-2 virus ORF1b and N genes amplified by oligonucleotide primers SEQ ID NOS:1 and 2, or 4 and 5, respectively, are also described.

Typically, each primer is present within an RT-qPCR reaction in a concentration of between about 0.1 μmol/L to about 1.0 μmol/L, preferably about 0.1 μmon. Typically, each probe is present within an RT-qPCR reaction in a concentration of between about 0.05 μmol/L to about 1.0 μmol/L, preferably about 0.25 μmon.

D. Compositions for RT-qPCR

In some forms, the RT-qPCR encompasses a two-step method, typically comprising two enzymes; the first step uses a RNA-dependent DNA polymerase, also known as a reverse transcriptase, to copy RNA into DNA (cDNA), the second step then switches to the use of DNA polymerase such as Taq polymerase, which amplifies the cDNA as in a standard PCR test.

In preferred forms, the reverse transcriptaion (RT) and the PCR reactions are carried out in a single test tube using fluorescence-based quantitative RT-PCR.

The described assay requires reagents and apparatus for conducting RT-qPCR procedures. Typically, test agents include buffer, RNA-dependent DNA polymerase, Taq polymerase, target-specific DNA primers, and a target-specific DNA probe that is labelled at one end with a fluorescent label and at the other with a quencher. In some forms, the target-specific DNA probe further comprises an internal quencher. Exemplary fluorescent labels on the target-specific DNA probe include FAM dyes, and exemplary quenchers on the target-specific DNA probe include internal ZEN® Quencher, Iowa Black FQ quenchers (IBFQ). In further preferred forms, the probes are double-quenched probes such as 5'FAM/ZEN/3'IBFQ.

In some forms, a typical reaction volume is from about 0.1 μL to about 1,000 μL, preferably about 20 μL. An exemplary monoplex RT-PCR reaction mixture includes 5 μL of 4× master reaction mixture (available from multiple commercial sources, such as TaqMan Fast Virus 1-Step Master Mix, from ThermoFisher), 0.5 μmol/L of forward primer, 0.5 μmol/L of reverse primer, 0.25 μmol/L of probe, and 4 μl of input sample. Typically, the assay is carried out within a thermal cycler or other apparatus suitable for conducting and monitoring necessary for conducting an RT-qPCR procedure. Suitable apparatus for conducting an RT-qPCR procedure are well known in the art and are available from multiple commercial sources, including the ViiA7 Real-Time PCR system from ThermoFisher.

III. Methods for Detecting and Quantifying SARS-CoV-2

Methods for detecting and quantifying SARS-CoV-2 nucleic acid in biological samples using a RT-qPCR system have been developed.

Early diagnosis is crucial for controlling the spread of COVID-19. Molecular detection of SARS-CoV-2 nucleic acid ORF1b and N genes are provided.

The detection time ranges from several minutes to hours. In preferred forms, the minimum number of copies of the target viral RNA required for identification of the SARS-CoV-2 virus within a sample is less than 10, for example, one two, three, four, five, six, seven, eight, nine, ten, or more than 10, such as 11, 12, 13, 14, 15, 16, 17, 18, 19, or 20 or more, 30, 40, 50, 60, 70, 80 or 100 or more.

The methods can detect SARS-CoV-2 in samples obtained from a variety of respiratory sources, including throat swabs, posterior oropharyngeal saliva, nasopharyngeal swabs, sputum and bronchial fluid, samples from the intestinal tract or blood. In some forms, the methods test for the presence of virus within two or more samples. In some forms, the methods detect virus in a sample of bodily fluid taken from a subject in whom the viral load is at the peak, or has not yet reached the peak, or has already drop from its peak level. In some forms, the methods also include one or more additional steps to confirm the result of a first assay. For example, in some forms, the methods detect the virus in a sample prior to, at the same time, or after the same sample is screened for the same or different virus, using one or more different techniques. Exemplary additional diagnostic techniques include CT scanning of the chests of subjects, and/or serological analyses, for example, tests detecting the presence of antibodies to one or more viral gene expression products, such as viral N or S proteins.

A. Quantitative PCR

Methods for detecting and quantifying SARS-CoV-2 nucleic acid from within biological samples using a RT-qPCR system are described. Methods for detecting the presence of SARS-CoV-2 within an input sample typically include a step of contacting RNA extracted from the input sample with a composition including (i) a set of primers configured to amplify one or more fragments of the SARS-CoV-2 virus;
(ii) a probe configured to bind to the amplified nucleic acid fragment; and
(iii) a RT-qPCR reaction mixture including reagents necessary for amplifying the one or more fragments of the SARS-CoV-2 virus.

The methods incubate the composition under conditions sufficient for an RT-qPCR reaction to amplify the one or more fragments of the SARS-CoV-2 virus to create an output sample.

The methods detect the one or more fragments of the SARS-CoV-2 virus and probe within the output sample,
wherein the presence of the one or more fragments of the SARS-CoV-2 virus and probe within the output sample identifies the input sample as containing SARS-CoV-2.

Typically, the contacting step occurs within a thermal cycler or other apparatus suitable for conducting and monitoring necessary for conducting an RT-qPCR procedure.

In some forms, the detecting step includes steps for quantifying and/or recording the number of copies of viral target RNAs within the sample.

In preferred forms, the composition of the contacting step includes (i) nucleic acid oligonucleotide primers corresponding to SEQ ID Nos 1-2, and (ii) a nucleic acid probe corresponding to SEQ ID NO. 3; and/or (i) nucleic acid oligonucleaotide primers corresponding to SEQ ID Nos 4-5, and (ii) a nucleic acid probe corresponding to SEQ ID NO. 6, respectively.

In preferred forms, the RT-qPCR is monoplex RT-qPCR. Exemplary reaction conditions include:

(1) reverse transcription at 50° C. for 5 mins,
(2) inactivation of reverse transcriptase at 95° C. for 20 secs,
(3) 40 cycles of PCR amplification including Denaturing at 95° C. for 5 secs and Annealing/Extending at 60° C. for 30 secs.

In some forms, the methods include recording the number of copies of viral target RNAs detected within the input sample in the detecting step. In some forms, the recording includes combining together with one or more additional pieces of datum relating to the input sample, or a subject or environment from which the input sample is derived. For example, in some forms, the recording includes annotating the number of copies of viral target RNAs within a sample together with one or more time points, such as the time post-exposure to the SARS-CoV-2 virus, and/or the time post onset of one or more symptoms of COVID-19. In some forms, the recording combines the data from two or more assays to form one or more databases. For example, in some forms, the recording annotates the number of copies of viral target RNAs within each of two or more input samples, together with one or more time points, such as the time post-exposure to the SARS-CoV-2 virus, and/or the time post onset of one or more symptoms of COVID-19 for each of two or more subjects from which each of the two or more input samples are derived. In some forms, the methods include combining the data from two or more assays with one or more pieces of data relating to a patient, such as the patient age, patient genetic background, disease symptoms, or other physiological or pathological information.

In some forms, the methods detect an amount of SARS-CoV-2 virus within an input sample derived from a patient, whereby the sample is obtained prior to the onset of COVID-19 symptoms in the patient. In some forms, the methods detect an amount of SARS-CoV-2 virus within an input sample derived from a patient, whereby the sample is collected within one, two, three, four, five, six, seven, eight, nine, or ten hours or days following the initial exposure of the patient to the SARS-CoV-2 virus.

In some forms, the methods include the additional step of determining the sequence of one or more of the genes of a SARS-CoV-2 virus within a sample identified as containing SARS-CoV-2. In some forms, the methods include one or more steps for recording the sequence data from one or more genes of one or more SARS-CoV-2 viruses within one or more databases, optionally together with one or more pieces of data relating the same or different samples.

In some forms, the methods include screening one or more positive and/or negative controls. Exemplary positive controls include one or more RNA sequences encoding one or more of the target viral RNAs. Exemplary positive control RNA sequences are include plasmids, or as cells expressing SARS-CoV-2 viruses, or DNA plasmids containing the target sequences. Exemplary negative controls include one or more RNA sequences specific for one or more distinct human respiratory pathogen.

In some forms, one or more of the method steps are performed together with one or more control samples. Exemplary distinct human respiratory pathogens for use as controls include human influenza A viruses (H1N1, H3N2, H5N1, and H7N9 subtypes), avian influenza (H1, H4, H6, and H9 subtypes), influenza B viruses. In some forms, one or more of the method steps are performed on a reagent blank.

In some forms, the methods include the step of treating a subject from whom an input sample has been obtained, whereby the SARS-CoV-2 virus is detected within the corresponding output RNA. In some forms, treatment is initiated prior to the onset of symptoms in the patient.

1. Two-Step RT-qPCR Assay

In some forms, the methods employ one RT-qPCR to screen a sample for the presence of the SARS-CoV-2 viral N gene (SEQ ID NO: 8), and then a second or further RT-qPCR to screen the same sample for the presence of the SARS-CoV-2 viral ORF1b gene (SEQ ID NO: 7), and/or additional viral RNAs. For example, in some forms, the methods employ a first RT-qPCR to detect the presence of the SARS-CoV-2 viral N gene (SEQ ID NO: 8) by detecting a fragment of the N gene amplified by oligonucleotide primers of SEQ ID NOs: 4 and 5, and labelled using an oligonucleotide probe of SEQ ID NO:6, and then the methods employ a second RT-qPCR to detect the presence of the SARS-CoV-2 viral ORF1b gene (SEQ ID NO: 7) in the same sample, by detecting a fragment of the ORF1b gene amplified by oligonucleotide primers of SEQ ID NOs: 1 and 2, and labelled using an oligonucleotide probe of SEQ ID NO. 3 Amplification of the viral N gene fragment informs the presence of the SARS-CoV-2 virus, and subsequent detection of the ORF1b gene fragment confirms the presence of the SARS-CoV-2 virus in the same sample. The detection of a single amplified gene fragment derived from the SARS-CoV-2 virus in either of a first or second RT-qPCR, without confirmation/amplification of the corresponding second gene fragment can warrant a second assay. In some forms, detection of a single amplified gene fragment without confirmation/amplification of the corresponding second gene fragment can indicate the presence of one or more genetic mutation or new variant of the SARS-CoV-2 virus within the sample. For example, the same or different assay can be carried out to confirm the presence of the SARS-CoV-2 virus in the sample, or to further characterize a variant SARS-CoV-2 virus. Exemplary methods for characterizing a variant of the SARS-CoV-2 virus include sequencing of the viral genome, and comparison of the sequence with that of other circulating viruses, such as the sequence of a SARS-CoV-2 virus set forth in GenBank accession number MN908947.3.

B. Use as a Diagnostic Assay

The described methods are useful for detecting the presence of the SARS-CoV-2 viruses within a sample obtained from a subject, such as a patient who is identified as having, or is suspected as having COVID-19. Therefore, in some forms, the methods diagnose a subject as having an infection with SARS-CoV-2 viruses, and/or having COVID-19.

In all of the described methods, the methods can include one or more steps of identifying a subject for screening according to the described sysmes for detecting the presence of the SARS-CoV-2 viruses within a sample obtained from the subject. Therefore, in some forms, the methods include a step for selecting a subject in need of screening for infection with a coronavirus. In further forms, the methods include one or more steps of obtaining one or more biological samples from the subject.

1. Diagnosis of COVID-19

The described methods are useful for diagnosing a patient as having COVID-19. In some forms, a subject is selected if they are suspected of being, or are identified as at risk of being infected with a coronavirus virus, for example, a SARS-CoV-2 virus. In some forms, subjects are selected based on one or more symptoms or other indications in the subject. In a preferred form, a subject has one or more symptoms or physiological markers of COVID-19. Symptoms of COVID-19 include but are not limited to fever, fatigue, dry cough, sputum production, headache, haemoptysis, diarrhoea, anorexia, sore throat, chest pain, chills, nausea, vomiting, dyspnoea, pneumonia, respiratory failure, septic shock, multiple organ dysfunction or failure and olfactory and taste disorders, such as loss or alteration of smell and/or taste. In some forms, subjects are asymptomatic. In some forms, asymptomatic subjects are selected without additional indications, for example, as apart of a community or population-wide screening process. In other forms, asymptomatic subjects are selected due to an increased risk of developing COVID-19, for example, due to potential exposure to SARS-CoV-2 virus or to proximity to infected individuals. In some forms, the same subject is repeatedly screened for the presence of SARS-CoV-2 viruses, for example, every day, week, month, or year.

In some forms the systems and methods detect the presence of SARS-CoV-2 virus in a biological sample that is a bodily fluid of a subject who has one or more symptoms or physiological markers of COVID-19, the bodily fluid including mucus, sputum (processed or unprocessed), bronchial alveolar lavage (BAL), bronchial wash (BW), bodily fluids, cerebrospinal fluid (CSF), urine, tissue (e.g., biopsy material), rectal swab, nasopharyngeal aspirate, nasopharyngeal swab, throat swab, feces, plasma, serum, and whole blood. The methods can include one or more steps of obtaining the biological sample from the subject. Exemplary methods for obtaining a biological sample from a subject suspected of having a respiratory disease include nasopharyngeal swab, nasopharyngeal aspiration, swab of sputa/deep throat saliva, and a throat swab of the subject. Additional methods for obtaining a biological sample from a subject include aspiration of blood, serum, exudate, pus and pleural fluid.

2. Epidemiology and Monitoring Vaccine Efficiacy

The described systems are useful for acquiring community or population-wide epidemiological information relating to the presence, spread and characteristics of circulating SARS-CoV-2 viruses. For example, in some forms, data obtained according to the described systems provide databases recording the prevalence of SARS-CoV-2 viruses within subjects in a community. Therefore, in some forms, a subject is selected based on one or more datum relating to the subject, such as geographical location, age, race, gender, or one or more genetic, phylogenetic, immunological, or serological criteria.

The described systems are also useful for acquiring community or population-wide information relating to the prevalence and characteristics of human immune responses to SARS-CoV-2 viruses. For example, in some forms, a subject is known to have no pre-existing immunity to one or more coronaviruses, and/or to one or more sarbecoviruses, and/or to one or more SARS-CoV-2 viruses. In other forms, a subject is known to have immunity to one or more coronaviruses, and/or to one or more sarbecoviruses, and/or to one or more SARS-CoV-2 viruses. In some forms, the subject has been vaccinated against one or more coronaviruses, and/or to one or more sarbecoviruses, and/or to one or more SARS-CoV-2 viruses. Therefore, in some forms, the data obtained according to the described methods provide information relating to the efficacy of one or more vaccines against SARS-CoV-2 viruses. In some forms, the subject has previously been infected with against one or more SARS-CoV-2 viruses, and/or has developed COVID-19.

IV. Kits

Kits are also disclosed. The kits can include, for example, a set of nucleic acid oligonucleaotide primers configured to amplify a fragment of the SARS-CoV-2 viral RNA, a nucleic acid probe configured to selectively bind and detect the fragment of the SARS-CoV-2 viral RNA amplified by the primers, and a RT-qPCR reaction mixture, including reagents and enzymes in an amount and concentration suitable for conducting at RT-qPCR. In an exemplary form, the kit includes one or more of a set of nucleic acid oligonucleotide primers corresponding to SEQ ID Nos 1-2, and a nucleic acid probe corresponding to SEQ ID NO. 3, and/or a set of nucleic acid oligonucleaotide primers corresponding to SEQ ID Nos 4-5, and a nucleic acid probe corresponding to SEQ ID NO. 6.

The kit can include two or more of the components, packaged separately or together in the same admixture. Each of the reagents can be supplied alone (e.g., lyophilized), or in a mixture composition. The active agents can be in a unit amount suitable for conducting a single monoplex RT-qPCR, or in a stock that should be diluted prior to use. In some forms, the kit includes a supply of buffers and reagents required for multiple RT-qPCR reactions. In some forms, the kit includes one or more positive and/or negative controls for the RT-qPCR amplification of SARS-CoV-2 viral RNA. The kit can also include devices for acquisition of biological samples, and/or for the extraction and purification of viral RNA from a biological sample. In some forms, the kit includes swabs for obtaining samples from the mouth, throat, nose and upper respiratory tract, syringes and/or pipettes. In some forms, the kit includes printed instructions for use of the reagents according to the methods described above.

The disclosed compositions and methods of using can be further understood through the following enumerated paragraphs.

1. A composition for the detection of SARS-CoV-2 virus N gene comprising PCR primers for amplifying a segment of the SARS-CoV-2 virus N gene comprising nucleotides corresponding to nucleotides 905-923 of SEQ ID NO:8.

2. The composition of paragraph 1, wherein the segment of the SARS-CoV-2 virus N gene comprising nucleotides corresponds to nucleotides 894-962 of SEQ ID NO:8.

3. The composition of paragraph 1, wherein the segment of the SARS-CoV-2 virus N gene comprising nucleotides corresponding to nucleotides 872-981 of SEQ ID NO:8.

4. The composition of any one of paragraphs 1-3, wherein the PCR primers comprise:

(i) a nucleic acid sequence consisting of SEQ ID NO:4 or a nucleic acid sequence having at least 90%, 95%, 96%, 97%, 98%, or 99% sequence identity to SEQ ID NO:4, and (ii) a nucleic acid sequence consisting of SEQ ID NO:5 or a nucleic acid sequence having at least 90%, 95%, 96%, 97%, 98%, or 99% sequence identity to SEQ ID NO:5.

5. A composition for the detection of SARS-CoV-2 virus ORF1b gene comprising PCR primers for amplifying a segment of the SARS-CoV-2 virus ORF1b gene comprising nucleotides corresponding to nucleotides 18547-18565 of SEQ ID NO:7.

6. The composition of paragraph 5, wherein the segment of the SARS-CoV-2 virus ORF1b gene comprising nucleotides corresponds to nucleotides 18536-18604 of SEQ ID NO:7.

7. The composition of paragraph 5, wherein the segment of the SARS-CoV-2 virus ORF1b gene comprising nucleotides corresponding to nucleotides 18514-18645 of SEQ ID NO:7.

8. The composition of any one of paragraphs 5-7, wherein the PCR primers comprise:
    (i) a nucleic acid sequence consisting of SEQ ID NO:1 or a nucleic acid sequence having at least 90%, 95%, 96%, 97%, 98%, or 99% sequence identity to SEQ ID NO:1, and
    (ii) a nucleic acid sequence consisting of SEQ ID NO:2 or a nucleic acid sequence having at least 90%, 95%, 96%, 97%, 98%, or 99% sequence identity to SEQ ID NO:2.

9. The composition of any one of paragraphs 1~4 further comprising a nucleic acid probe having one or more fluorescent reporters, one or more quenchers, or a combination thereof,
    wherein the probe is configured to specifically bind to a nucleic acid sequence within SEQ ID NO:8.

10. The composition of paragraph 9, wherein the probe is configured to specifically bind to a segment of the SARS-CoV-2 virus N gene comprising nucleotides corresponding to nucleotides 905-923 of SEQ ID NO:8.

11. The composition of paragraph 9, wherein the probe is configured to specifically bind to a segment of the SARS-CoV-2 virus N gene comprising nucleotides corresponding to nucleotides 894-962 of SEQ ID NO:8.

12. The composition of paragraph 9, wherein the probe is configured to specifically bind to a segment of the SARS-CoV-2 virus N gene comprising nucleotides corresponding to nucleotides 872-981 of SEQ ID NO:8.

13. The composition of paragraph 9, wherein the nucleic acid probe has a nucleic acid sequence consisting of SEQ ID NO:6 or a nucleic acid sequence having at least 90%, 95%, 96%, 97%, 98%, or 99% sequence identity to SEQ ID NO:6.

14. The composition of any one of paragraphs 2-8, further comprising a nucleic acid probe having one or more fluorescent reporters, one or more quenchers, or a combination thereof,
    wherein the probe is configured to specifically bind to a nucleic acid sequence within SEQ ID NO:7.

15. The composition of paragraph 14, wherein the probe is configured to specifically bind to a segment of the SARS-CoV-2 virus ORF1b gene comprising nucleotides corresponding to nucleotides 18547-18565 of SEQ ID NO:7.

16. The composition of paragraph 14, wherein the probe is configured to specifically bind to a segment of the SARS-CoV-2 virus ORF1b gene comprising nucleotides corresponding to nucleotides 18536-18604 of SEQ ID NO:7.

17. The composition of paragraph 14, wherein the probe is configured to specifically bind to a segment of the SARS-CoV-2 virus ORF1b gene comprising nucleotides corresponding to nucleotides 18514-18645 of SEQ ID NO:7.

18. The composition of paragraph 14, wherein the nucleic acid probe has a nucleic acid sequence consisting of SEQ ID NO:3 or a nucleic acid sequence having at least 90%, 95%, 96%, 97%, 98%, or 99% sequence identity to SEQ ID NO:3.

19. The composition of any one of paragraphs 1~4 or 9-13 further comprising one or more of a phosphate buffer, a Tris buffer, a potassium salt, a sodium salt, a magnesium salt, an ammonium salt, dATP, dCTP, dGTP, and dTTP, a reverse transcriptase enzyme, and a DNA polymerase enzyme.

20. The composition of paragraph 19, wherein the salt is selected from the group consisting of KCl, NaCl, $MgCl_2$, $MgSO_4$, $(NH_4)_2SO_4$.

21. The composition of paragraph 19, wherein the DNA polymerase is Taq polymerase.

22. A method of detecting the presence of SARS-CoV-2 nucleic acid in an input sample, comprising:
    (a) contacting the input sample with the composition of paragraph 9 under conditions sufficient for amplification of one or more regions of the N gene of SARS-CoV-2,
    wherein detection of the SARS-CoV-2 N gene amplification product indicates the presence of SARS-CoV-2 in the input sample.

23. The method of paragraph 22, wherein the amplification comprises a reverse transcription quantitative polymerase chain reaction (RT-qPCR).

24. The method of paragraph 22, wherein the input sample comprises purified nucleic acids.

25. The method of paragraph 24, wherein the method includes a step of extracting nucleic acids from a biological sample to create the input sample.

26. The method of paragraph 25, wherein the biological sample is a bodily fluid of a subject, the bodily fluid selected from the group consisting of mucus, sputum (processed or unprocessed), bronchial alveolar lavage (BAL), bronchial wash (BW), bodily fluids, cerebrospinal fluid (CSF), urine, tissue (e.g., biopsy material), rectal swab, nasopharyngeal aspirate, nasopharyngeal swab, throat swab, feces, plasma, serum, and whole blood.

27. The method of paragraph 26, wherein the method further comprises a step of obtaining the biological sample from the subject.

28. The method of paragraph 27, wherein the biological sample is obtained from a nasopharyngeal swab, a nasopharyngeal aspirate, sputa/deep throat saliva or a throat swab of the subject.

29. The method of paragraph 26, wherein the subject is selected from the group consisting of a subject who has one or more symptoms of COVID-19, an asymptomatic subject who is at increased risk of being infected with SARS-CoV-2 virus, a subject who has received a vaccine against infection with SARS-CoV-2 virus, and a deceased subject.

30. The method of paragraph 22, wherein the input sample contains 10 or more copies of the SARS-CoV-2 N gene.

31. The method of paragraph 22 further comprising (b) contacting the input sample with the composition of paragraph 13 under conditions sufficient for amplification of one or more regions of the ORF1b gene of SARS-CoV-2, wherein detection the SARS-CoV-2 ORF1b gene amplification product indicates the presence of SARS-CoV-2 in the input sample.

32. The method of paragraph 31, wherein the input sample contains 10 or more copies of the SARS-CoV-2 ORF1b gene.

The present invention is further understood by reference to the following non-limiting examples.

EXAMPLES

Example 1: Development of RT-qPCR Assay for Identification of Virus within Biological Samples

Materials and Methods

Primer and Probe Sequences

Two monoplex real-time RT-PCR assays targeting the ORF1b and N gene regions of 2019-nCoV were designed based on the first publicly available sequence in Genbank (Accession number: MN908947). The downloaded sequence and those for SARS coronavirus, bat SARS-like coronaviruses, and other representative coronaviruses were edited and aligned. Phylogenetic analyses of these sequences were performed using the neighbor joining method in MEGA X. Two sequence regions (ORF1b and N) that are highly conserved amongst sarbecoviruses were selected for primer and probe designs.

The primer and probe sequences for the ORF1b gene assay are:

```
                              (SEQ ID NO: 1)
5'-TGGGGYTTTACRGGTAACCT-3'
(Forward; Y = C/T, R¹/₄AA/G), (SEQ ID NO: 2)
5'-AACRCGCTTAACAAAGCACTC-3'
(Reverse; R = A/G),
and (SEQ ID NO: 3)
5'-TAGTTGTGATGCWATCATGACTAG-3'
(Probe in 5'-FAM/ZEN/3'-
IBFQ format; W = A/T).
```

The primer and probe sequences for the N gene assay are:

```
                              (SEQ ID NO: 4)
5'-TAATCAGACAAGGAACTGATTA-3'
(Forward), (SEQ ID NO: 5)
5'-CGAAGGTGTGACTTCCATG-3'
(Reverse)
and (SEQ ID NO: 6)
5'-GCAAATTGTGCAATTTGCGG-3'
(Probe in 5'-FAM/ZEN/3'-IBFQ
format).
```

The expected amplicon sizes of ORF1b and N gene assays are 132 bp and 110 bp, respectively. All primers and probes were purchased from a commercial source (Integrated DNA Technologies). The primer and probe sequences were subsequently confirmed to have perfect matches with other 2019-nCOV genome sequences available from Global Initiative on Sharing All Influenza Data (GISAID; gisaid.org/ Accession numbers: EPI_ISL_402119, EPI_ISL_402120, EPI_ISL_402121, EPI_ISL_402123 and EPI_ISL_402124; Accessed 12 Jan. 2020).

Quantitative Reverse Transcriptase PCR (RT-qPCR) Assay Conditions

A typical 20 mL monoplex RT-PCR assay contained 5 µl L of 4× master reaction mixture (TaqMan Fast Virus 1-Step Master Mix, ThermoFisher), 0.5 µmol/L of forward primer, 0.5 µmol/L of reverse primer, 0.25 µmol/L of probe, and 4 µl of RNA sample.

RT-PCR reactions were conducted by a thermal cycler (ViiA7 Real-Time PCR system, ThermoFisher) with the following conditions:

Reverse transcription at 50° C. for 5 min;

Inactivation of reverse transcriptase at 95° C. for 20 s;

40 cycles of PCR amplification (Denaturing at 95° C. for 5 s; Annealing/Extending at 60° C. for 30 s).

The time for each RT-PCR run was about 1 h and 15 min.

Viral RNA purification kit (QIAamp Viral RNA Mini Kit, Qiagen) and DNA plasmid purification kit (QIAprep Spin Miniprep Kit, Qiagen) were used for RNA and DNA extractions, respectively, as instructed by the manufacturer. For all RNA extractions, RNA was extracted from 140 µL of sample and eluted in 60 µL elution buffer containing poly(A) carrier RNA.

Tested Samples

Clinical samples for molecular tests are recommended to be handled using biosafety level 2 practices. As SARS coronavirus is classified as a biosafety level 3 (BSL3) pathogen, DNA plasmids were used as positive controls in these tests. This can avoid distributing SARS coronavirus genomic RNA which has the potential of generating infectious clones via reverse genetics. In addition, this can also help to distribute positive controls to laboratories at different geographical regions in a more cost-effective and robust manner.

Viral RNA extracted from SARS coronavirus-infected cells was used for positive controls. In addition, the RTPCR products of SARS coronavirus generated by the ORF1b and N gene assays were cloned into plasmids. Serially diluted RNA or DNA samples were used to evaluate the performance of these assays. To determine the specificity of these assays, negative control samples were tested. These negative control samples were: 1) RNA extracted from cultured viruses: human coronaviruses (229E, OC43, and MERS), camel coronavirus (HKU23), human influenza A viruses (H1N1, H3N2, H5N1, and H7N9 subtypes), avian influenza (H1, H4, H6, and H9 subtypes), influenza B viruses (Yamagata and Victoria lineages), and adenovirus, 2) RNA extracted from retrospective human respiratory specimens previously tested positive for coronavirus (229E, HKU1, NL63, OC43), influenza A viruses (H1N1 and H3N2 subtypes), influenza B viruses (Yamagata and Victoria lineages), adenovirus, enterovirus, human parainfluenza virus (PIV1, 2, 3 and 4), respiratory syncytial virus, human metapneumovirus, rhinovirus and human bocavirus, and 3) RNA extracted from sputum samples from patients without respiratory viral infections (n=9). Culture supernatants of infected cells or clinical samples stored in standard virus transport media were subjected to a brief centrifugation (15,170×g, 2 min) and 140 µL of supernatant from each sample was used for RNA extraction.

Two patients (Patients 1 and 2) suspected to be infected by 2019-nCoV in Beijing were included in this study. For Patient 1, a sputum sample was collected at day 5 post-onset of symptoms. The sputum sample stored in standard virus transport media was treated with an equal volume of Sputasol (ThermoFisher) before RNA extraction. For Patient 2, a throat swab sample was collected at day 3 post-onset of symptoms and stored in standard virus transport media. 140 µL of each aqueous sample was used for viral RNA extraction. Relevant clinical and epidemiological data for both patients were not accessible to this study. RNA extracted from these samples were serially diluted and tested by the assays.

Results

Specificity of the Assays

At the time of preparing this assay, there was only one viral sequence available from the public domain. With such a limited sequence information, we decided to develop two RT-PCR assays that can react with multiple coronaviruses that are in the subgenus Sarbecovirus. Using additional sequence information from this clade of coronaviruses, we selected highly conserved ORF1b and N gene regions as our targets (FIGS. 1A and 1B). These designs allow the use of nucleic acids derived from SARS coronavirus as positive controls.

Figure 2A:
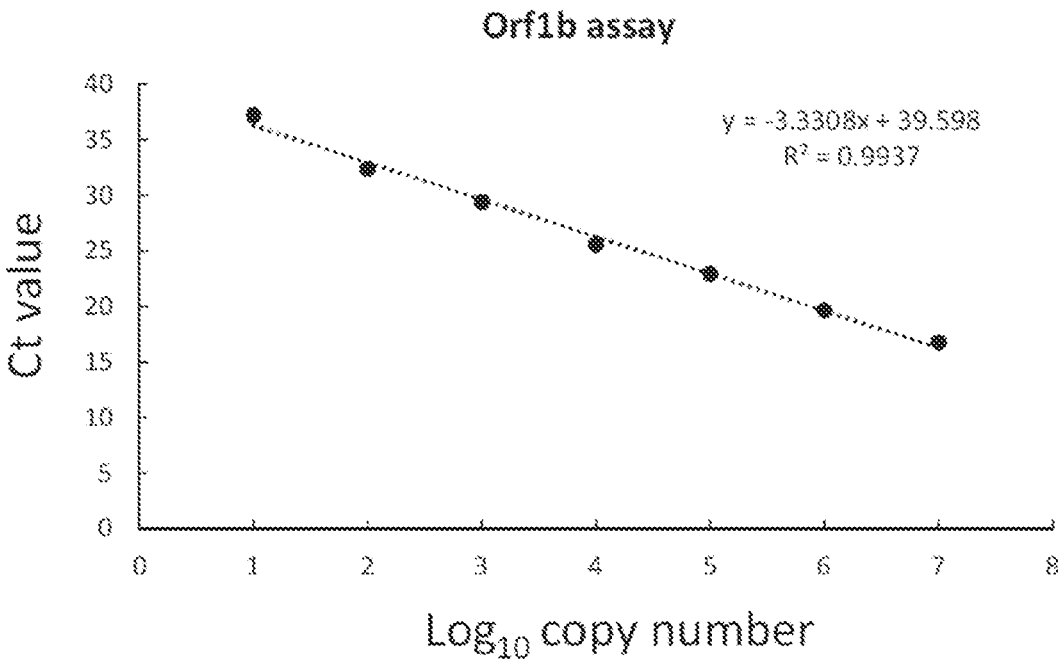
FIGS. 2A-2B are dot-plot graphs, showing Ct value (0-40) over Log 10 copy number (0-8) for each of the ORF-1b gene assay (FIG. 2A) and the N gene assay (FIG. 2B), respectively.
Figure 2B:
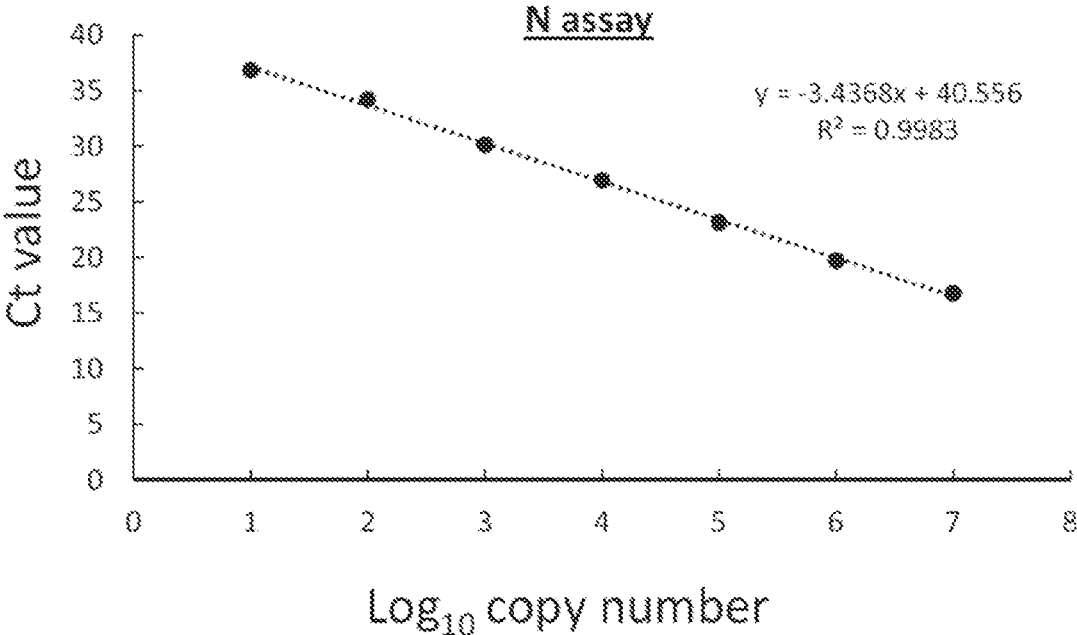

Evaluation of the Assays using Viral RNA Extracted from Positive and Negative Control Samples Viral RNA from cells infected by SARS coronavirus or DNA plasmids containing the target sequences were positive in the assays as expected. Using viral RNA extracted from virus cultures with known titers, both assays have a dynamic range of at least seven orders of magnitude ($2 \times 10^{-4}$-2000 $TCID_{50}$/reaction; data not shown). To accurately determine the detection limits of these assays, we also tested serially diluted positive control plasmids in these assays. In our preliminary trial, reactions with >10 copies of this positive control. Plasmid were consistently positive in both of the assays (n=5). The DNA amplifications of these newly established assays were found to be efficient. The amplification efficiencies of ORF1b and N gene assays were 99.6% and 95.4%, respectively (FIGS. 2A and 2B, $R^2$>0.99 in both cases).

All negative controls were found to be negative in these assays (data not shown). In addition, we also spiked known amounts of SARS coronavirus into representative negative control samples (10-fold serially diluted virus sample; range: $2 \times 10^{-4}$-2000 $TCID_{50}$/reaction; Number of tests per concentration: 1). RNA extracted from these spiked samples were all positive in the tests, with no significant RT-PCR inhibition detected.

Detection of COVID-19 in Patient Samples

Respiratory specimens from two suspected patients were tested by both RT-PCR assays. Both patients were positive in the tests (Table 1). Preliminary results from serially diluted RNA samples suggested that the N gene assay is about 10 times more sensitive than the ORF-1b gene assay in detecting positive clinical specimens. As these samples could only be tested qualitatively by these assays at the testing site, the exact viral copy numbers in these specimens cannot be determined.

TABLE 1

Detection of 2019-nCoV in patient samples

| Dilution | Assay (Ct value) | |
| --- | --- | --- |
| | Orf1b* | N* |
| Patient 1 | | |
| Neat | 28.79 | 30.96 |
| 10x | 31.935 | 33.83 |
| 100x | Neg | 36.9 |
| 1000x | Neg | Neg |
| 10000x | Neg | Neg |
| Patient 2 | | |
| Neat | 22.10 | 24.14 |
| 10x | 25.66 | 28.02 |
| 100x | 29.33 | 31.33 |
| 1000x | 32.55 | 34.54 |
| 10000x | Neg | 37.70 |

*Single test results at each dilution

Summary

In summary, two assays targeting the viruses in the subgenus Sarbecovirus were made and evaluated as being reactive to multiple viruses in the subgenus. This is because there is insufficient public information about the genetic diversity of 2019-nCoV in humans and animals In 2003, SARS coronaviruses found in palm civets and humans were genetically highly similar, but distinct. For example, a partial deletion was detected in SARS coronavirus found in palm civets. Similar subtle sequence variations were also observed in MERS coronavirus found in camels and humans To avoid the possible scenario in which the genetic diversity of 2019-nCoV is much more diverse than appreciated, the primer and probe sets were designed to react with this clade of coronaviruses.

The assays were evaluated using a panel of positive and negative control samples. The assays were found to be sensitive and specific to only sarbecoviruses. Respiratory specimens from patients infected by 2019-nCoV were used to demonstrate the potential use of these tests. The tested clinical samples were different in nature (sputum vs. throat swab) and they were collected at different onset times (day 5 vs. day 3). Nonetheless, the results demonstrated the clinical value of these respiratory samples for molecular detection of 2019-nCoV. In addition, the N gene RTPCR assay was found to be more sensitive in detecting 2019-nCoV RNA in the studied clinical samples. It is possible that these clinical samples might contain infected cells expressing subgenomic RNA, resulting in more N gene copies in the samples.

With the exception of 2019-nCoV and SARS coronavirus, none of the sarbecoviruses have been previously detected in humans. SARS was eliminated in humans and the last reported human SARS case was detected in 2004. Individuals with samples that are positive in these RT-PCR assays should be considered as having been infected by the 2019-nCoV or its related animal coronaviruses. Based on their detection performances, the N gene RT-PCR is recommended as a screening assay, and the Orf1b assay is recommended as a confirmatory one. Using a diagnostic algorithm similar to MERS, an N gene positive/Orf1b negative result should be regarded as indeterminate, and the case is recommended to be referred to a WHO reference lab for further testing. In the event of having positive PCR results, sequence analyses of positive amplicons can help to confirm the result and to distinguish between 2019-nCoV and other genetically related coronaviruses (e.g., SARS coronavirus).

REFERENCES

1. Cui et al., *Nat Rev Microbiol* 2019; 17:181-92.
2. Donnelly et al., *Emerg Infect Dis* 2019; 25:1758-60.
3. Poon et al., *Lancet Infect Dis* 2004; 4:663-71.
4. Hemida et al., *Euro Surveill* 2013; 18:20659.
5. Reusken, et al. *Euro Surveill* 2013; 18:20662.
6. Guan et al., *Science* 2003; 302:276-8.
7. de Wit E, et al., *Nat Rev Microbiol* 2016; 14:523-34.
8. Chan et al., *mBio* 2013; 4:e00191-13.
9. Hu, et al., *PLoS Pathog* 2017; 13:e1006698.
10. World Health Organization. Novel Coronavirus (2019-nCoV), Situation report-1. webpage who.int/docs/default-source/coronaviruse/situation-reports/20200121-sitrep-1-2019-ncov.pdf?sfvrsn=20a99c10_4 (Accessed January 2020).
11. Zhou, et al. Preprint at webpage biorxiv.org/content/10.1101/2020.01.22.914952v1 (2020).
12. World Health Organization. Novel Coronavirus (2019-nCoV), Situation report-2. webpage who.int/docs/default-source/coronaviruse/situation-reports/20200122-sitrep-2-2019-ncov.pdf? sfvrsn=4d5bcbca_2 (Accessed January 2020).
13. South China Morning Post. webpage scmp.com/news/china/society/article/3046908/new-china-virus-likely-human-transmissionstage-infections. (Accessed January 2020).
14. Kumar et al., *Mol Biol Evol* 2018; 35:1547-9.
15. Chu et al., *Proc Natl Acad Sci USA* 2018; 115:3144-9.
16. Simons et al., *J Virol Methods* 2005; 124:111-6.
17. Wang, et al. *Emerg Infect Dis* 2005; 11:1860-5.
18. World Health Organization. webpage who.int/docs/default-source/coronaviruse/peiris-protocol-16-1-20.pdf?sfvrsn=af1aac73_4/(Accessed January 2020).
19. World Health Organization. webpagewho.int/publications-detail/laboratory-testing-for-2019-novel-coronavirus-(2019-nCoV)-insuspected-human-cases (Accessed January 2020).
20. Corman et al., *Euro Surveill* 2020; 25:pii=2000045.

We claim:

1. A composition for the detection of SARS-CoV-2 virus N gene comprising PCR primers for amplifying a segment of the SARS-CoV-2 virus N gene comprising nucleotides corresponding to nucleotides 905-923, 894-962, or 872-981 of SEQ ID NO:8.

2. The composition of claim 1, wherein the PCR primers comprise:
 (i) a nucleic acid sequence consisting of SEQ ID NO:4 or a nucleic acid sequence having at least 90%, 95%, 96%, 97%, 98%, or 99% sequence identity to SEQ ID NO:4, and
 (ii) a nucleic acid sequence consisting of SEQ ID NO:5 or a nucleic acid sequence having at least 90%, 95%, 96%, 97%, 98%, or 99% sequence identity to SEQ ID NO:5.

3. A composition for the detection of SARS-COV-2 virus ORF1b gene comprising PCR primers for amplifying a segment of the SARS-COV-2 virus ORF1b gene comprising nucleotides corresponding to nucleotides 18547-18565, 18536-18604, or 18514-18645 of SEQ ID NO:7.

4. The composition of claim 3, wherein the PCR primers comprise:
 (i) a nucleic acid sequence consisting of SEQ ID NO: 1 or a nucleic acid sequence having at least 90%, 95%, 96%, 97%, 98%, or 99% sequence identity to SEQ ID NO:1, and
 (ii) a nucleic acid sequence consisting of SEQ ID NO:2 or a nucleic acid sequence having at least 90%, 95%, 96%, 97%, 98%, or 99% sequence identity to SEQ ID NO:2.

5. The composition of claim 1, further comprising a nucleic acid probe having one or more fluorescent reporters, one or more quenchers, or a combination thereof, wherein the probe is configured to specifically bind to a nucleic acid sequence within SEQ ID NO:8, optionally within nucleotides 905-923, 894-962, or 872-981 of SEQ ID NO:8.

6. The composition of claim 5, wherein the nucleic acid probe has a nucleic acid sequence consisting of SEQ ID NO:6 or a nucleic acid sequence having at least 90%, 95%, 96%, 97%, 98%, or 99% sequence identity to SEQ ID NO:6.

7. The composition of claim 1, further comprising a nucleic acid probe having one or more fluorescent reporters, one or more quenchers, or a combination thereof, wherein the probe is configured to specifically bind to a nucleic acid sequence within SEQ ID NO:7, optionally within nucleotides 18547-18565, 18536-18604, or 18514-18645 of SEQ ID NO:7.

8. The composition of claim 7, wherein the nucleic acid probe has a nucleic acid sequence consisting of SEQ ID NO:3 or a nucleic acid sequence having at least 90%, 95%, 96%, 97%, 98%, or 99% sequence identity to SEQ ID NO:3.

9. The composition of claim 1 further comprising one or more of a phosphate buffer, a Tris buffer, a potassium salt, a sodium salt, a magnesium salt, an ammonium salt, dATP, dCTP, dGTP, and dTTP, a reverse transcriptase enzyme, and a DNA polymerase enzyme.

10. The composition of claim 9, wherein the salt is selected from the group consisting of KCl, NaCl, MgCl$_2$, MgSO$_4$, and (NH$_4$)$_2$SO$_4$.

11. The composition of claim 9, wherein the DNA polymerase is Taq polymerase.

12. A method of detecting the presence of SARS-COV-2 nucleic acid in an input sample, comprising:
 (a) contacting the input sample with the composition of claim 5 under conditions sufficient for amplification of one or more regions of the N gene of SARS-COV-2, wherein detection of the SARS-COV-2 N gene amplification product indicates the presence of SARS-COV-2 in the input sample.

13. The method of claim 12, wherein the amplification comprises a reverse transcription quantitative polymerase chain reaction (RT-qPCR).

14. The method of claim 12, wherein the input sample comprises purified nucleic acids.

15. The method of claim 14, wherein the method includes a step of extracting nucleic acids from a biological sample to create the input sample.

16. The method of claim 15, wherein the biological sample is a bodily fluid of a subject, the bodily fluid selected from the group consisting of mucus, sputum (processed or unprocessed), bronchial alveolar lavage (BAL), bronchial wash (BW), bodily fluids, cerebrospinal fluid (CSF), urine, tissue, rectal swab, nasopharyngeal aspirate, nasopharyngeal swab, throat swab, feces, plasma, serum, and whole blood.

17. The method of claim 16, wherein the method further comprises a step of obtaining the biological sample from the subject, optionally wherein the subject is selected from the group consisting of a subject who has one or more symptoms of COVID-19, an asymptomatic subject who is at increased risk of being infected with SARS-COV-2 virus, a subject who has received a vaccine against infection with SARS-COV-2 virus, and a deceased subject.

18. The method of claim 12, wherein the input sample contains 10 or more copies of the SARS-COV-2 N gene.

19. The method of claim 12 further comprising
 (b) contacting the input sample with the composition of claim 6 under conditions sufficient for amplification of one or more regions of the ORF1b gene of SARS-COV-2, wherein detection the SARS-COV-2 ORF1b gene amplification product indicates the presence of SARS-COV-2 in the input sample.

20. The method of claim 19, wherein the input sample contains 10 or more copies of the SARS-COV-2 ORF1b gene.

* * * * *